United States Patent [19]
Haskell et al.

[11] 4,311,698
[45] Jan. 19, 1982

[54] AMINOACID DERIVATIVES OF CEPHALOSPORIN COMPOUNDS

[76] Inventors: Theodore H. Haskell, 3860 Loch Alpine Dr. W.; Thomas F. Mich, 915 Sunset Rd., both of Ann Arbor, Mich. 48103; Dietrich Schweiss, 7136 Plymouth Rd.; Townley P. Culbertson, 2996 Argonne, both of Ann Arbor, Mich. 48105

[21] Appl. No.: 112,655

[22] Filed: Jan. 31, 1980

Related U.S. Application Data

[63] Continuation-in-part of Ser. No. 19,983, Mar. 12, 1979, abandoned.

[51] Int. Cl.$^3$ .............. A61K 31/545; C07D 501/34; C07D 501/56
[52] U.S. Cl. .................................. 424/246; 544/22; 544/27; 544/28; 546/298
[58] Field of Search .......................... 544/28, 22, 27; 424/246

[56] References Cited

U.S. PATENT DOCUMENTS 3,954,734  5/1976  Doub et al. ..................... 544/28

Primary Examiner—Paul M. Coughlan, Jr.

[57] ABSTRACT

Novel organic amide compounds which are N-[6-[(acylaminoacylamino or aminoacylamino)phenyl]-1,2-dihydro-2-oxonicotinyl]cephalosporin compounds having broad spectrum antibacterial utility are provided by (a) reacting the free amino acid of the appropriate cephalosporin or the acid salt or silylated derivative or complex thereof with a reactive derivative of the corresponding N-6-[(acylaminoacylamino or aminoacylamino)phenyl]-1,2-dihydro-2-oxonicotinic acid or (b) reacting the free amino acid 7-aminocephalosporanic acid or a related compound or the acid salt or silylated derivative thereof with a reactive derivative of the corresponding D-N-[6-(acylaminoacylamino or aminoacylamino)phenyl]-1,2-dihydro-2-oxonicotinyl]-2-substituted glycine. Pharmaceutical compositions containing said compounds and methods for treating infections using said compositions are also disclosed.

52 Claims, No Drawings

AMINOACID DERIVATIVES OF CEPHALOSPORIN COMPOUNDS

This is a continuation-in-part of copending U.S. application, Ser. No. 19,983, filed Mar. 12, 1979, now abandoned.

SUMMARY AND DETAILED DESCRIPTION

The present invention relates to novel chemical compounds that are useful as pharmacological agents and to methods for their production. More particularly, the invention relates to novel organic amide compounds having the formula

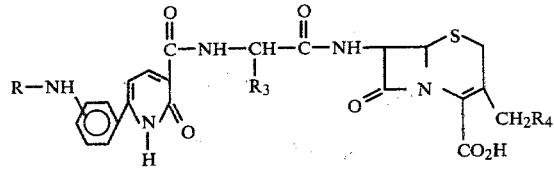

and pharmaceutically acceptable salts thereof; wherein R is

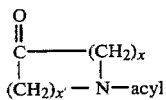

or $R_1\text{-}[R_5N\text{-}acyl]_n$; x is an integer of from one to five; $x'$ is zero, one or two, $R_1$ is hydrogen, lower alkyl, benzyl or

wherein $R_2$ is hydrogen, amino or a lower alkyl group of from one to four carbon atoms optionally substituted by from one to three chlorine or fluorine atoms, $R_5$ is hydrogen or lower alkyl and N-acyl is an aminoacyl moiety derived from a carboxylic acid of from two to ten carbon atoms, optionally substituted by from one to three of the following groups, hydroxyl, carboxyl,

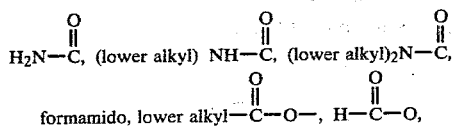

amino, lower alkylamino, carbamido, carbonyl oxygen, lower alkoxy, lower alkylthio or sulfonic acid, n is an integer of from one to four; $R_3$ is phenyl, 4-hydroxyphenyl, 2-thienyl or cyclohexa-1,4-dien-1-yl and $R_4$ is acetoxy, carbamoyloxy, or a heterocyclicthio group where the heterocyclic moiety is an optionally methyl substituted thiadiazolyl, triazolyl or tetrazolyl group or the heterocyclicthio group has the formula

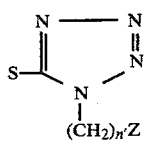

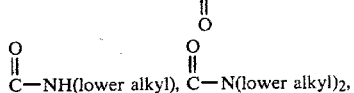

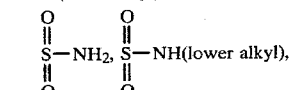

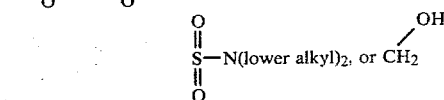

and $n'$ is an integer of from one to four.

When n is two to four the acyl groups may be the same or different. When the acyl group is substituted by more than one group, the substituents may be the same or different.

Included within the above definition for N-acyl are cyclic structures incorporating the nitrogen atom by displacement of the hydrogen atom, such as the pyroglutamyl group, prolyl group, etc.

The carbon atoms may be part of a configuration which is classified as an aliphatic, olefinic or aromatic grouping or mixture of both, such as a phenethyl group.

The preferred compounds are those wherein R—NH is in the p position and is an optically active aminoacyl fragment. The most preferred compounds are those wherein N-acyl is D-alanyl, L-glutaminyl, D-glutaminyl, L-pyroglutamyl, L-lysyl; $R_2$ is a carbon fragment of from one to four carbon atoms, $R_3$ is phenyl or p-hydroxyphenyl, $R_4$ is acetoxy; and pharmaceutically acceptable salts thereof.

Lower alkyl, where not specifically defined, is defined as a hydrocarbon fragment of from one to six carbon atoms. Lower alkoxy is equivalent to "lower alkyl—O—".

In accordance with the invention the foregoing amide compounds having the formula

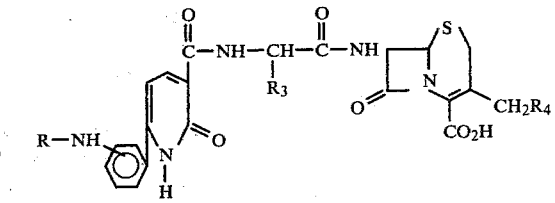

and pharmaceutically acceptable salts thereof wherein R, $R_3$ and $R_4$ are as previously defined are produced by reacting a compound of the formula

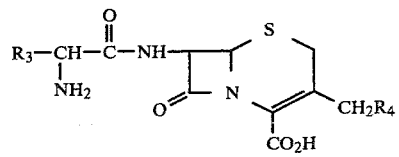

or the basic salt, silylated derivative (preferably the disilylated) thereof with a reactive derivative of a 1,2-dihydro-2-oxonicotinic acid compound having the formula

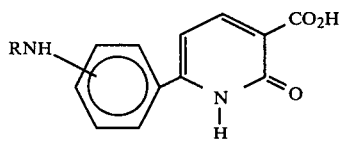

or its acid addition salt.

Some examples of reactive derivatives of the 6-(substituted)-1,2-dihydro-2-oxonicotinic acid compound suitable for the reaction are the acid halides (especially the acid chloride), the imidazolide, mixed anhydrides (especially those formed from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the cephalosporin compounds in the zwitter ionic salt form, aqueous solutions may be used for acylation with an acid halide or mixed anhydride under normal Schotten-Baumann conditions. The duration and temperature of the reaction are not critical. Temperatures in the range from −30° to +30° are commonly used for reaction times ranging from a few hours up to a day or more. The product may be isolated in any suitable way as the free acid or as a salt by appropriate adjustment of the pH.

The reactive derivative of 6-(substituted)-1,2-dihydro-2-oxonicotinic acid compounds and acid-addition salts which are required as starting materials in the foregoing process can be prepared according to any of a variety of methods.

A 6-(substituted)-1,2-dihydro-2-oxonicotinic acid may be converted to its acid chloride utilizing thionyl chloride, its mixed anhydride utilizing ethyl chloroformate, its pentachlorophenyl ester by esterification with pentachlorophenol in the presence of dicyclohexylcarbodiimide and its imidazolide be reacting the acid with 1,1'-carbonyldiimidazole.

Compounds of the formula

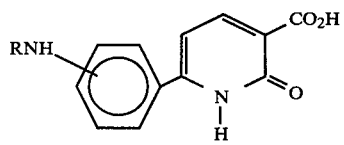

wherein $R_1[NH\text{-acyl}]_n$ is as previously defined except where $R_1$ is hydrogen are prepared by acylation of a compound of the formula by a compound of the formula

R—OH wherein R is $H[NR_5\text{-acyl}]_n$

The compound of the formula

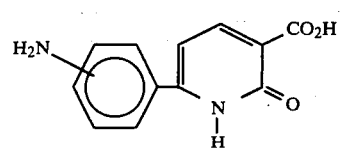

is prepared by hydrolyzing a compound of the formula

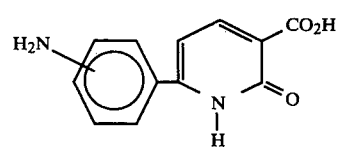

which is in turn prepared by coupling a compound of the formula

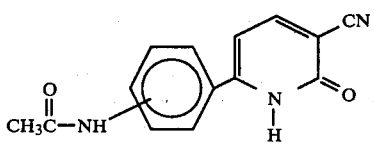

in the form of an alkali metal salt, preferably sodium, with 2-cyanoacetamide.

The compound of the formula

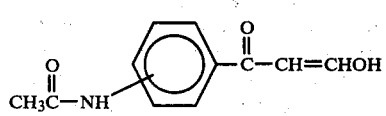

in the form of its alkali metal salt, preferably sodium, is prepared by formylating a compound of the formula

The silylated amino acid starting materials can be prepared by reacting an amino acid of the formula

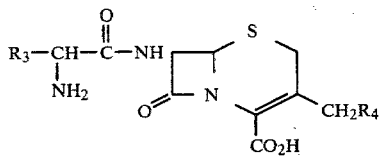

or a salt thereof wherein $R_3$ is as previously defined in anhydrous form with either one or two equivalents of a tri (lower alkyl) silyl chloride in the presence of triethylamine. The preferred silylating agents are trimethylsilyl chloride and dimethyl dichlorosilane. In all probability when two equivalents of the silylating agent are used, both the amino and the carboxyl group become silylated. When one equivalent is used, only the carboxyl group is silylated. Both the mono-and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

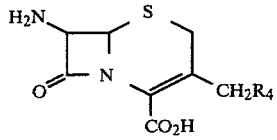

or the corresponding acid salt or silylated derivative thereof with a reactive derivative of D-N-[6-substituted)-1,2-dihydro-2-oxonicotinyl]-2-substituted glycine having the formula

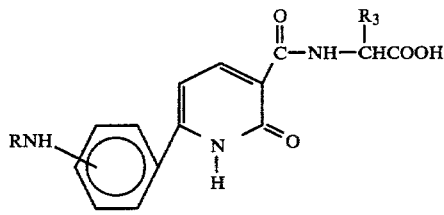

or its acid addition salts where R, $R_3$ and $R_4$ have the aforementioned significance.

Some examples of reactive derivatives of the D-N-(1,2-dihydro-2-oxonicotinyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 7-aminocephalosporanic acid may be reacted with an acid chloride or mixed anhydride in the free acid or salt form using aqueous solutions under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of D-N-[6-(substituted)-1,2-dihydro-2-oxonicotinyl]-2-substituted glycines or their acid-addition salts which are required as starting materials in the foregoing process can be prepared by methods illustrated in greater detail hereinafter.

D-N-[6-(substituted)]-1,2-dihydro-2-oxonicotinyl]-2-substituted glycine compounds may be prepared by reacting the corresponding reactive derivative of 6-(substituted)-1,2-dihydro-2-oxonicotinic acid, such as acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

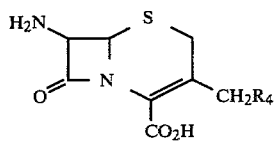

with a hexaalkyldisilazane. The preferred silylating agent is hexamethyldisilazane. In all probability, only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, lithium hydroxide, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. Certain compounds are capable of forming di-salts, which is dependent upon the final pH of the solution. In addition, certain of the compounds of the invention can exist in the form of an acid-addition salt. Pharmaceutically acceptable salts are formed by reaction of the free base of a carboxylate salt (zwitter ion) with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic, and related acids.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The pyridone segment of the compounds of this invention may be capable of undergoing keto-enol tautomerism to give 2-hydroxypyridines. Such a tautomer is equivalent to the pyridones for the purposes of the inventions and are included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof. Even when a specific form is cited, small amounts of its stereoisomer may be present, since racemization may occur during the various steps in preparing the compound.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

ACTIVITY TABLE

Minimal Inhibitory Concentration (μg/ml)

| A sodium salt of a compound of Example | Structure | Pseudomonas BRK 12-4-4 | Pseudomonas UI 18 | E. Coli Brig | E. Coli Vogel | Prot Vulg. | Entero Cloac. IM 11 | Serr. Mar. IMM 16 | Klebs. Pneum. MGH 2 | Strep. fec. MGH 2 | Staph UC76 | Staph S 18713 |
|---|---|---|---|---|---|---|---|---|---|---|---|---|
| 1. | Ac Ala NH— (D), pyridone-phenyl-C(O)—N—S-tetrazole-CH$_2$CO$_2$Na | #28 6.3 | 6.3 | 6.3 | 0.4 | 3.1 | 3.1 | 12.5 | 3.1 | >50 | 3.1 | 12.5 |
| 20. | Ac Ala NH— (L), pyridone-phenyl-C(O)—N—S-tetrazole-CH$_3$ | 12.5 | 12.5 | 6.3 | 1.6 | 12.5 | 6.3 | 25 | 1.6 | 25 | 1.6 | 3.1 |
| 11. | Ac NH—C(CH$_3$)$_2$—C(O)—NH— pyridone-phenyl-C(O)—C.G. | 3.1 | 6.3 | 12.5 | 3.1 | 12.5 | 12.5 | 50 | 12.5 | 25 | 0.4 | 3.1 |
| 22. | Ac Ala NH— (DL), pyridone-phenyl-C(O)—N—S-thiazole-CH$_3$ | 12.5 | 12.5 | 6.3 | 1.6 | 12.5 | 12.5 | 25 | 3.1 | 12.5 | 0.4 | 6.3 |
| 28. | Ac Ala NH— (D), pyridone-phenyl-C(O)—C.G. | 12.5 | 25 | 25 | 12.5 | 50 | 50 | >50 | 25 | 25 | 1.6 | 1.6 |
| 3. | Ac Ala NH— (DL), pyridone-phenyl-C(O)—C.G. | 12.5 | 12.5 | 12.5 | 3.1 | 25 | 25 | 25 | 6.3 | 25 | 0.4 | 1.6 |

-continued
ACTIVITY TABLE
Minimal Inhibitory Concentration (μg/ml)

| Example | A sodium salt of a compound of | Pseudomonas | | | E. Coli. | | Prot | Entero Cloac. | Serr. Mar. | Klebs. Pneum. | Strep. fec. | | Staph |
|---|---|---|---|---|---|---|---|---|---|---|---|---|---|
| | | #28 | BRK 12-4-4 | UI 18 | Brig | Vogel | Vulg. | IM 11 | IMM 16 | MGH 2 | MGH 2 | UC76 | S 18713 |
| 5. | Ac Ala NH—⟨phenyl⟩—pyridone—C(O)—C.G. (L) | 6.3 | 12.5 | 6.3 | 12.5 | 1.6 | 25 | 12.5 | 50 | 12.5 | 25 | 0.8 | 1.6 |
| 18 | Ac Ala NH—⟨phenyl⟩—pyridone—C(O)—Z—S—tetrazole-CH₃ (DL) | 6.3 | 12.5 | 6.3 | 3.1 | 0.4 | 25 | 6.3 | 12.5 | 0.8 | 25 | 0.4 | 3.1 |
| 6. | Pyrrolidinone-C(O)—NH—⟨phenyl⟩—pyridone—C(O)—C.G. (L) | 12.5 | 12.5 | 6.3 | 12.5 | 3.1 | 25 | 12.5 | 50 | 6.3 | 25 | 0.8 | 3.1 |
| 4. | AcNHCH(CH₃)—C(O)—NH—⟨phenyl⟩—pyridone—C(O)—C.G. (D) | 6.3 | 12.5 | 6.3 | 6.3 | 3.1 | 25 | 12.5 | 50 | 6.3 | 25 | 0.8 | 1.6 |
| 19. | AcNH CH(CH₃)—C(O)—NH—⟨phenyl⟩—pyridone—C(O)—Z—S—tetrazole-CH₃ (D) | 6.3 | 12.5 | 12.5 | 6.3 | 0.8 | 12.5 | 12.5 | 25 | 3.1 | 25 | 0.8 | 6.3 |
| 24. | AcNH CH(CH₃)—C(O)—NH—⟨phenyl⟩—pyridone—C(O)—Z—O—C(O)—NH₂ (D) | 12.5 | 12.5 | 12.5 | 25 | 6.3 | 12.5 | 25 | >50 | 12.5 | 25 | 0.4 | 1.6 |

ACTIVITY TABLE
Minimal Inhibitory Concentration (μg/ml)
| A sodium salt of a compound of Example | Structure | Pseudomonas #28 | Pseudomonas BRK 12-4.4 | Pseudomonas UI 18 | E. Coli. Brig | E. Coli. Vogel | Prot Vulg. | Entero Cloac. IM 11 | Serr. Mar. IMM 16 | Klebs. Pneum. MGH 2 | Strep. fec. MGH 2 | Staph UC76 | Staph S 18713 |
|---|---|---|---|---|---|---|---|---|---|---|---|---|---|
| 29. |  | 1.6 | 1.6 | 1.6 | 6.3 | 1.6 | 6.3 | 12.5 | 25 | 6.3 | 12.5 | 0.4 | 1.6 |
| 8. | 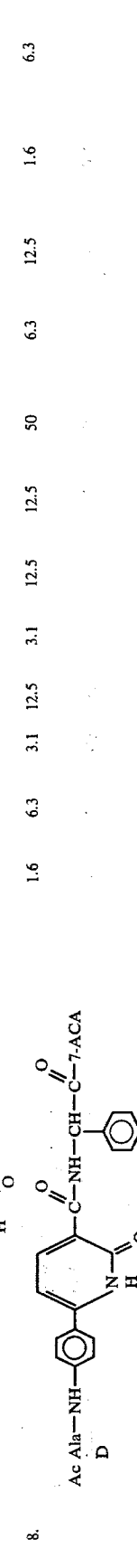 | 1.6 | 6.3 | 3.1 | 12.5 | 3.1 | 12.5 | 12.5 | 50 | 6.3 | 12.5 | 1.6 | 6.3 |
| 14. | 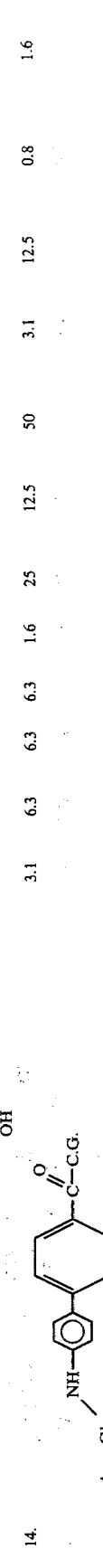 | 3.1 | 6.3 | 6.3 | 6.3 | 1.6 | 25 | 12.5 | 50 | 3.1 | 12.5 | 0.8 | 1.6 |
| 9. | 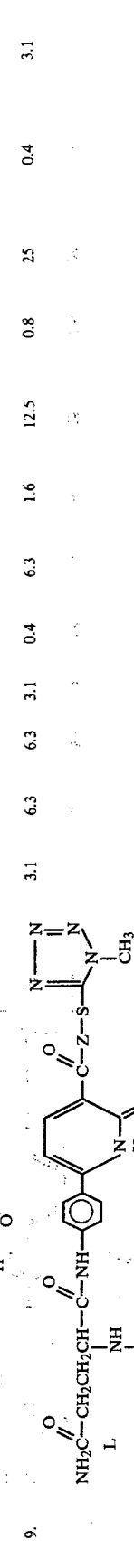 | 3.1 | 6.3 | 6.3 | 3.1 | 0.4 | 6.3 | 1.6 | 12.5 | 0.8 | 25 | 0.4 | 3.1 |
| 10. | 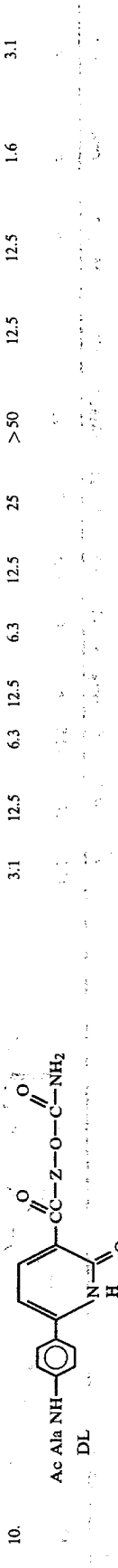 | 3.1 | 12.5 | 6.3 | 12.5 | 6.3 | 12.5 | 25 | >50 | 12.5 | 12.5 | 1.6 | 3.1 |
| 25. | 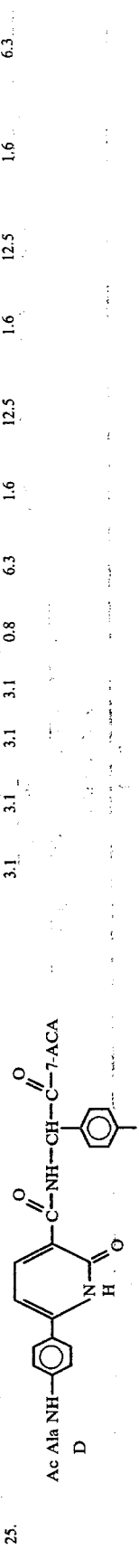 | 3.1 | 3.1 | 3.1 | 3.1 | 0.8 | 6.3 | 1.6 | 12.5 | 1.6 | 12.5 | 1.6 | 6.3 |

-continued

ACTIVITY TABLE

Minimal Inhibitory Concentration (μg/ml)

| A sodium salt of a compound of Example | Structure | Pseudomonas #28 | BRK 12-4-4 | UI 18 | E. Coli. Brig | E. Coli. Vogel | Prot Vulg. | Entero Cloac. IM 11 | Serr. Mar. IMM 16 | Klebs. Pneum. MGH 2 | Strep. fec. MGH 2 | UC76 | Staph S 18713 |
|---|---|---|---|---|---|---|---|---|---|---|---|---|---|
| 15. | Ac Ala NH— ... L | 12.5 | 12.5 | 12.5 | 6.3 | 1.6 | 12.5 | 12.5 | 25 | 3.1 | 12.5 | 0.4 | 6.3 |
| 23.* | NH₂C—CH₂CHC—NH— ... D Ac NH | 12.5 | 6.3 | 6.3 | 3.1 | 0.8 | 12.5 | 6.3 | 25 | 1.6 | 25 | 0.8 | 6.3 |
| 13. | NH₂C—CH₂CHC—NH— ... Ac NH | 12.5 | 12.5 | 6.3 | 12.5 | 3.1 | 25 | 12.5 | >50 | 6.3 | 25 | 0.8 | 6.3 |
| 12. | pyrrolidine-Ac L | 6.3 | 12.5 | 6.3 | 6.3 | 3.1 | 25 | 12.5 | 50 | 6.3 | 12.5 | 0.8 | 3.1 |
| 17. | pyrrolidine-Ac DL | 12.5 | 25 | 12.5 | 25 | 3.1 | 25 | 25 | 50 | 12.5 | 50 | 1.6 | 3.1 |
| 2. | pyrrolidine-Ac L | 12.5 | 25 | 12.5 | 6.3 | 1.6 | 25 | 6.3 | 12.5 | 1.6 | 25 | 0.8 | 3.1 |

-continued

ACTIVITY TABLE
Minimal Inhibitory Concentration (µg/ml)

| A sodium salt of a compound of Example | Structure | Pseudomonas BRK #28 | Pseudomonas BRK 12-4-4 | UI 18 | E. Coli. Brig | E. Coli. Vogel | Prot Vulg. | Entero Cloac. IM 11 | Serr. Mar. IMM 16 | Klebs. Pneum. MGH 2 | Strep. fec. MGH 2 | UC76 | Staph S 18713 |
|---|---|---|---|---|---|---|---|---|---|---|---|---|---|
| 7. | (structure with L-pyroglutamyl, aminophenyl-pyridinone, methyl-tetrazolethio) | 6.3 | 6.3 | 6.3 | 3.1 | 0.8 | 12.5 | 3.1 | 12.5 | 1.6 | 12.5 | 0.4 | 3.1 |
| 27. | DiAcLysine NH DL (C.G. structure, methyl-tetrazolethio) | 3.1 | 12.5 | 6.3 | 25 | 3.1 | 50 | 12.5 | >50 | 6.3 | 25 | 1.6 | 12.5 |
| 26. | DiAcLysine NH DL (pyridinone structure, methyl-tetrazolethio) | 12.5 | 12.5 | 12.5 | 12.5 | 1.6 | 25 | 6.3 | 50 | 1.6 | 50 | 1.6 | 6.3 |
| 16. | L (pyroglutamyl, aminophenyl-pyridinone, CH₂CO₂Na-tetrazolethio) | 3.1 | 6.3 | 6.3 | 3.1 | 0.4 | 0.4 | 3.1 | 6.3 | 0.8 | 50 | 3.1 | 12.5 |
| 21. | AcGlutamine NH (CH₂CO₂Na-tetrazolethio) | 6.3 | 12.5 | 6.3 | 3.1 | 3.1 | 3.1 | 6.3 | 12.5 | 3.1 | 50 | 6.3 | 25 |
| 30. | Ac Hypro NH L (CH₂CO₂Na-tetrazolethio) | 6.3 | 12.5 | 6.3 | 3.1 | 0.8 | 1.6 | 3.1 | 12.5 | 1.6 | >50 | 6.3 | 25 |

-continued
ACTIVITY TABLE
Minimal Inhibitory Concentration (µg/ml)

| A sodium salt of a compound of Example | Structure | Pseudomonas | | | E. Coli. | | Prot Vulg. | Entero Cloac. IM 11 | Serr. Mar. IMM 16 | Klebs. Pneum. MGH 2 | Strep. fec. MGH 2 | Staph | |
|---|---|---|---|---|---|---|---|---|---|---|---|---|---|
| | | #28 | BRK 12-4-4 | UI 18 | Brig | Vogel | | | | | | UC76 | S 18713 |
| 34. | (structure with succinimide-CH3, L) | 6.3 | 12.5 | 6.3 | 12.5 | 3.1 | 12.5 | 12.5 | 50 | 6.3 | 25 | 0.4 | 3.1 |
| 32. | AcO-pyrrolidine-Ac, L | 12.5 | 25 | 12.5 | 25 | 6.3 | 25 | 25 | >50 | 12.5 | 25 | 1.6 | 6.3 |
| 41. | Ac Ala NH, D, CH2CH2CO2Na | 6.3 | 12.5 | 12.5 | 6.3 | 0.8 | 3.1 | 6.3 | 12.5 | 1.6 | 50 | 3.1 | 12.5 |
| 37. | Ac Gln NH, D, CH2CO2Na | 6.3 | 6.3 | 6.3 | 6.3 | 0.8 | 3.1 | 6.3 | 12.5 | 3.1 | >50 | 6.3 | 25 |
| 42. | Ac Gln NH, L, CH2SO3Na | 12.5 | 6.3 | 6.3 | 6.3 | 0.8 | 3.1 | 6.3 | 12.5 | .3.1 | >50 | 6.3 | 12.5 |
| 35. | Di Ac Lys NH, L | 12.5 | 12.5 | 6.3 | 25 | 6.3 | >50 | 12.5 | >50 | 12.5 | 25 | 3.1 | 6.3 |

-continued
ACTIVITY TABLE
Minimal Inhibitory Concentration (μg/ml)
| | Pseudomonas | | | E. Coli. | | Prot Vulg. | Entero Cloac. IM 11 | Serr. Mar. IMM 16 | Klebs. Pneum. MGH 2 | Strep. fec. MGH 2 | Staph | |
|---|---|---|---|---|---|---|---|---|---|---|---|---|
| A sodium salt of a compound of Example | #28 | BRK 12-4-4 | UI 18 | Brig | Vogel | | | | | | UC76 | S 18713 |
| 31. | 12.5 | 12.5 | 12.5 | 12.5 | 3.1 | 25 | 12.5 | >50 | 6.3 | 25 | 0.8 | 25 |
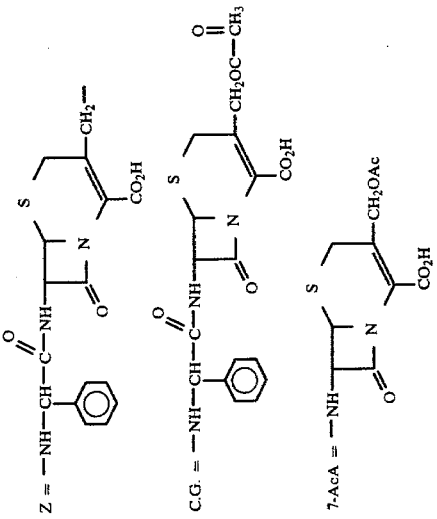
*A lithium salt of a compound of Example 23

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 30 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

EXAMPLE 1

N-[6-[4-(N-Acetyl-D-alanylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A suspension of 3.4 g (5.5 m mol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979 (1977)], 2.0 g (5 m mol) of Starting Material B, and 25 ml of N,N-dimethylacetamide is stirred at room temperature and 1.4 ml (10 m mol) of triethylamine is added dropwise during a 20 min period. The resulting solution is stirred at room temperature for 3 hrs and 0.91 ml (6.5 m mol) of triethylamine is added. The solution is poured in a thin stream into 300 ml of stirring ethyl acetate. The precipitate is filtered, washed with ethyl acetate and dried at 0.1 mm over phosphorus pentoxide. The product is dissolved in 300 ml of cold water and the pH is adjusted to 2.1 with 1 N hydrochloric acid. The precipitated acid is filtered, washed with 0.01 N hydrochloric acid and suspended in 150 ml of ice water. The pH is brought to 6.9 with 1 N sodium hydroxide and the solution clarified by filtration. The filtrate is lyophilized to give 4.3 g of the disodium salt of the above named final product; $[\alpha]_D^{23} -268°$ (cl, pH 7).

$$E_1^1 = 283 \ \lambda \ 358 \ nm \atop E_1^1 = 193 \ \lambda \ 265 \ nm \ \text{pH 7}$$

EXAMPLE 2

N-[6-[4-(N-Acetyl-L-prolylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid.

A mixture of 2.8 g (6 m mol) of 7-[D-2-amino-2-phenylacetamido]-3-[[(1-methyl-1H-tetrazol-5-yl)thio]methyl]-3-cephem-4-carboxylic acid [J. Antibiot., 29, 65 (1976)], 2.5 g (6 m mol) of Starting Material E, and 25 ml of N,N-dimethylacetamide is stirred at room temperature for 4 hrs and 1.82 ml (6 m mol) of a 3.3 M solution of sodium 2-ethylhexanoate in N,N-dimethylacetamide is added. The reaction solution is poured in a thin stream into 300 ml of stirring ethyl acetate. The precipitate is filtered, washed with ethyl acetate, and dried at 0.1 mm over phosphorus pentoxide to give 5.1 g of crude product. The solid is dissolved in 300 ml of ice water and the pH is adjusted to 2.5 with 1 N hydrochloric acid. The solid is filtered, washed with ice water, suspended in 150 ml of ice water, and the pH brought to 7 with 1 N sodium hydroxide. The solution is clarified by filtration and lyophilized to give 4.5 g of the sodium salt of the title cephalosporin derivative; $[\alpha]_D^{23} -103°$ (cl, pH 7).

$$E_1^1 = 337 \ \lambda \ 358 \ nm \atop E_1^1 = 220 \ \lambda \ 265 \ nm \ \text{pH 7}$$

EXAMPLE 3

N-[6-[4-(N-Acetyl-DL-alanylamino)phenyl]-1,2-dihydro-2-oxonicotinyl]-7-[D-2-amino-2-phenylacetamido]-3-acetoxymethyl cephem-4-carboxylic acid.

A suspension of 2.05 g (5 m mol) of cephaloglycin, 1.96 g (5 m mol) of Starting Material H, 25 ml of N,N-dimethylacetamide, and 25 ml of DMSO is stirred at room temperature for 4 hrs. The mixture is filtered and 1.5 ml (5 m mol) of 3.3 M sodium 2-ethylhexanoate in N,N-dimethylacetamide is added to the filtrate. The solution is added dropwise to a stirred solution of 300 ml of ethyl acetate and 50 ml of ether. The precipitate is collected and washed with ethyl acetate and ether. The solids are dissolved in 100 ml of cold water and the pH adjusted to 2.5 with hydrochloric acid. The resulting solids are filtered, washed with water, and suspended in cold water. The pH is brought to 7.5 with 1 N sodium hydroxide and the solution clarified by filtration. The filtrate is lyophilized to give 3.04 g of the sodium salt of the above named final product; $[\alpha]_D^{23} -437°$ (cl, pH 7).

$$E_1^1 = 390 \ \lambda \ 357 \ nm \atop E_1^1 = 230 \ \lambda \ 262 \ nm \ \text{pH 7}$$

EXAMPLE 4

N-[6-[4-(N-Acetyl-D-alanylamino)phenyl]-1,2-dihydro-2-oxonicotinyl]-7-[D-2-amino-2-phenylacetamido]-3-acetoxymethyl-3-cephem-4-carboxylic acid.

The D-alanyl compound is prepared by the method of Example 3 using the imidazolide of 6-]4-(N-acetyl-D-alanyl)aminophenyl]-1,2-dihydro-2-oxonicotinic acid, (Starting Material B). The compound is isolated as the sodium salt of the above named cephalosporin derivative; $[\alpha]_D^{23} -440°$ (cl, pH 7).

$$E_1^1 = 395 \ \lambda \ 358 \ nm \atop E_1^1 = 239 \ \lambda \ 262 \ nm \ \text{pH 7}$$

EXAMPLE 5

N-[6-[4-(N-Acetyl-L-alanylamino)phenyl]-1,2-dihydro-2-oxonicotinyl]-6-[D-2-amino-2-phenylacetamido]-3-acetoxymethyl-3-cephem-4-carboxylic acid.

The L-alanyl compound is prepared by the method of Example 3 using the imidazolide of 6-[4-(N-Acetyl-L-alanyl)aminophenyl]-1,2-dihydro-2-oxonicotinic acid, (Starting Material I). The compound is isolated as the sodium salt of the above named cephalosporin derivative; $[\alpha]_D^{23} -286°$ (cl, pH 7).

$$E_1^1 = 355 \ \lambda \ 358 \ nm \atop E_1^1 = 214 \ \lambda \ 261 \ nm$$

EXAMPLE 6

N-[6-[4-(L-Pyroglutamylamino)phenyl]-1,2-dihydro-2-oxonicotinyl]-7-[D-2-amino-2-phenylacetamido]-3-acetoxymethyl-3-cephem-4-carboxylic acid.

A mixture of 2.5 g (6.05 m mol) of cephaloglycin, 2.15 g (5.5 m mol) of Starting Material L, 50 ml of N,N-dimethylacetamide and 0.77 ml (5.5 m mol) of triethylamine is stirred at 0°–5°* for 1 hr and then at room temperature for 3 hrs. The suspension is filtered and 2.5 ml (8.3 m mol) of 3.27 M sodium 2-ethylhexanoate in N,N-dimethylacetamide is added. The solution is added dropwise to 700 ml of stirred ethyl acetate. The resulting precipitate is stirred for 10 min and filtered, washed with ethyl acetate and dried. The solid is dissolved in 100 ml of ice water and the pH adjusted from 7.5 to 2.5 with 1 N hydrochloric acid. The solid is filtered and suspended in 100 ml of water, stirred for 20 min and filtered. The acid is resuspended in 100 ml of ice water and the pH is adjusted to 6.5 with 1 N sodium hydroxide. Filtration and lyophilization of the filtrate gives 2.2 g of crude product. The material is dissolved in 10 ml of water and 90 ml of acetone is added. The precipitate is discarded and the solution is further diluted with 210 ml of acetone. This precipitate is collected and dissolved in 50 ml of water and lyophilized to give 1.66 g of the sodium salt of the above named cephalosporin derivative; $[\alpha]_D^{23} -88°$ (cl, pH 7).

$$E_1^1 = 326 \; \lambda \; 358 \text{ nm} \atop = 213 \; \lambda \; 258 \text{ nm} \; \text{pH 7}$$

*All temperatures are shown in degrees Centigrade.

EXAMPLE 7

N-[6-[4-(L-Pyroglutamylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid.

A mixture of 3.46 g (7.2 m mol) of 7-[D-2-amino-2-phenylacetamido]-3-[[(1-methyl-1H-tetrazol-5yl)thio]methyl]-3-cephem-4-carboxylic acid [J. Antibiot., 29, 65 (1976)], 2.35 g (6 m mol) of Starting Material L, and 25 ml of N,N-dimethylacetamide is stirred at 0°–5° for 15 min and at room temperature for 2 hrs 15 min. The reaction mixture is filtered and 2.2 ml (7.2 m mol) of 3.27 M sodium 2-ethylhexanoate in N,N-dimethylacetamide is added to the filtrate. The resulting solution is added to 500 ml of rapidly stirred ethyl acetate, filtered, washed with ethyl acetate and dried to give 4.86 g yellow solid. The crude material is dissolved in 150 ml of ice water and the pH adjusted to 2.8 with 1 N hydrochloric acid. The precipitate is filtered washed with water, suspended in ice water and the pH is adjusted to 7 with 1 N sodium hydroxide. The resulting solution is clarified by filtration and lyophilized to give 4.2 g of solid. The compound is further purified using preparative high pressure liquid chromatography on a Waters Associates Prep Pak 500 C-18 reverse phase column, using 80:20 water:acetonitrile as elution solvent. Lyophilization of the appropriate fractions gives 1.3 g of the sodium salt of the above named cephalosporin; $[\alpha]_D^{23} +19.5°$ (cl, pH 7)

$$E_1^1 = 369 \; \lambda \; 358 \text{ nm} \atop = 249 \; \lambda \; 267 \text{ nm} \; \text{pH 7}$$

EXAMPLE 8

N-[6-[4-(N-Acetyl-D-alanylamino)phenyl]-1,2-dihydro-2-oxonicotinyl]-7-[D-2-amino-2-(4-hydroxyphenyl)acetamido]-3-acetoxymethyl-3-cephem-4-carboxylic acid.

Using the method of Example 15, 3.0 g (5.6 m mol) of 7-[D-2-amino-2-(4-hydroxyphenyl)acetamido]-3-acetyloxy-3-cephem-4-carboxylic acid trifluoroacetic acid salt, 2.0 g (5.1 m mol) of Starting Material B, 1.7 ml (5.6 m mol) of 3.3 M sodium 2-ethylhexanoate in N,N-dimethylacetamide, 15 ml of N,N-dimethylacetamide, and 15 ml of DMSO are allowed to react at room temperature for 1.5 hrs. Work up with 1.7 ml (5.6 m mol) of 3.3 M sodium-2-ethylhexanoate in N,N-dimethylacetamide and lyophilization of a pH 7.4 solution gives 3.5 g of the sodium salt of the above named final product; $[\alpha]_D^{23} +62.5°$ (cl, pH 7.5).

$$E_1^1 = 358 \; \lambda \; 358 \text{ nm} \atop = 218 \; \lambda \; 262 \text{ nm} \; \text{pH 7}$$

EXAMPLE 9

N-[6-[4-(N-Acetyl-L-glutaminylamino)phenyl]-1,2-dihydro-2-oxonicotinyl]-7-(D-2-amino-2-phenylacetamido]-3-[[(1-methyl-1H-tetrazol-5-yl)thio]methyl]-3-cephem-4-carboxylic acid.

A solution of 82.6 g (0.11 mol) of 7-[D-2-amino-2-phenylacetamido]-3-[[(1-methyl-1H-tetrazol-5yl)thio]methyl]-3-cephem-4-carboxylic acid (salt with 1.5 eq of p-toluenesulfonic acid) [J. Antibiot., 29, 65 (1976), U.S. Pat. No. 3,769,281], 45 g of (0.1 mol) of Starting Material D, and 500 ml of N,N-dimethylacetamide is stirred at 0°–5° C. for 30 min and at room temperature for 2 hrs. The reaction mixture is treated with 64 ml (0.204 mol) of 3.2 M sodium 2-ethylhexanoate in N,N-dimethylacetamide and the resulting solution poured into 2 L of rapidly stirring ethyl acetate. The solid is filtered, washed with ethyl acetate and ether and air dried. The powder is dissolved in 1.25 L of water at 15° and the pH is adjusted to 2.0 with 6 N hydrochloric acid. The solid is filtered, washed with water and resuspended in 2.5 L of water and dissolved by adjusting the pH of 6.7 with 1 N sodium hydroxide. The solution is clarified by filtration and lyophilized to give 82.8 g of the sodium salt of the above cephalosporin; $[\alpha]^{23} -212.4°$ (cl, pH 7).

$$E_1^1 = 325 \; \lambda \; 357 \text{ nm} \atop = 209 \; \lambda \; 266 \text{ nm}$$

EXAMPLE 10

N-[6-[4(N-Acetyl-DL-alanylamino)phenyl]-1,2-dihydro-2-oxonicotinyl]-7-[D-2-amino-2-phenylacetamido]-3-carbamoyloxymethyl-3-cephem-4-carboxylic acid.

A solution of 1.90 g (3.65 m mol) of 7-[D-2-amino-2-phenylacetamido]-3-carbamoyloxymethyl-3-cephem-4-carboxylic acid triluoroacetic acide salt [Belgium Pat. No. 835,238] and 10 ml of N,N-dimethylacetamide is stirred at room temperature and 1.40 g (3.56 m mol) of Starting Material H is added. The reaction is stirred at room temperature for 4 hrs and 3 ml (9.8 m mol) of 3.27 M sodium 2-ethylhexanoate in N,N-dimethylacetamide is added and stirring is continued for 15 min. The solution is added dropwise to 150 ml of ethyl acetate and the precipitate is filtered, washed with ethyl acetate and dried to give 3.25 g of crude product. The solid is dissolved in 100 ml of ice water and filtered. The pH of the filtrate is taken to 2.5 with 1 N hydrochloric acid and the solids filtered. The solid is suspended in 150 ml of water and dissolved by adjusting the pH to 7.3 with 1 N sodium hydroxide. The solution is clarified by filtration and lyophilized to give 2.5 g of sodium salt of the above named cephalosporin derivative; $[\alpha]_D^{23} -256°$ (cl, pH 7).

$$E_1^1 = 374 \lambda\ 358\ nm\ pH\ 7$$
$$E_1^1 = 226 \lambda\ 262\ nm$$

EXAMPLE 11

N-[6-[4-(N-Acetyl-alpha-aminoisobutyrylamino)-phenyl]-1,2-dihydro-2-oxonicotinyl]-7-[D-2-amino-2-phenylacetamido]-3-acetoxymethyl-3-cephem-4-carboxylic acid.

A suspension of 4.1 g (10 m mol) of cephaloglycin and 50 ml of N,N-dimethylacetamide is stirred at 0°–5° and 3.2 g (7.8 m mol) of Starting Material C is added followed by 1.4 ml (10 m mol) of triethylamine. The cooling bath is removed and the reaction mixture stirred at room temperature for 4 hrs and is filtered. The filtrate is cooled and 3.45 ml (10 m mol) of 2.9 M sodium 2-ethylhexanoate is added. The solution is added dropwise to 600 ml of stirring ethyl acetate at 5°. The resulting mixture is stirred for 20 min and the solids filtered and washed with ether and dissolved in 200 ml of water. The solution is acidified to pH 2.5 with 1 N hydrochloric acid and the solids are separated by filtration, washed with water and resuspended in 100 ml of cold water. The pH is adjusted to 6.5 with 1 N sodium hydroxide and the solution lyophilized to give 4.9 g of the sodium salt of the title cephalosporin derivative; $[\alpha]_D^{23} +8.5°$ (cl, pH 7).

$$E_1^1 = 377 \lambda\ 358\ nm\ pH\ 7$$
$$E_1^1 = 221 \lambda\ 259\ nm$$

EXAMPLE 12

N-[6-[4-(N-Acetyl-L-prolylamino)phenyl]-1,2-dihydro-2-oxonicotinyl]-7-[D-2-amino-2-phenylacetamido]-3-acetoxymethyl-3-cephem-4-carboxylic acid.

A suspension of 3.22 g (7.87 m mol) of cephaloglycin, 3.0 (7.15 m mol) of Starting Material E and 25 m of N,N-dimethylacetamide is stirred at 0°–5° and 1.0 ml (7.15 m mol) of triethylamine is added. The mixture is stirred in the cold for 2.5 hrs and is poured into 500 ml of ice water. The pH is adjusted to 2.8 with 1 N hydrochloric acid and the yellow solid is filtered. The acid is suspended in ice water and stirred for 20 min and filtered. The solids are resuspended in 100 ml of ice water and the pH adjusted to 7.0 with 1 N sodium hydroxide. Filtration and lyophilization of the filtrate gives 4.0 g of the sodium salt of the title compound; $[\alpha]_D^{23} -269°$ (cl, pH 7).

$$E_1^1 = 404 \lambda\ 358\ nm\ pH\ 7$$
$$E_1^1 = 240 \lambda\ 261\ nm$$

EXAMPLE 13

N-[6-[4-(N-Acetyl-D-aspariginylamino)phenyl]-1,2-dihydro-2-oxonicotinyl]-7-[D-2-amino-2-phenylacetamido]-3-acetoxymethyl-3-cephem-4-carboxylic acid.

A mixture of 2.52 g (6 m mol) of cephaloglycin, 2.62 g (6 m mol) of Starting Material G, 15 ml of N,N-dimethylacetamide and 15 ml DMSO is stirred at room temperature for 3 hrs. A small amount of insoluble material is filtered and 1.82 ml (6 m mol) 3.3 M sodium 2-ethylhexanoate in N,N-dimethylacetamide is added. The solution is poured into 300 ml of ethyl acetate, stirred for 15 min, and filtered. The solids are washed with ethyl acetate and ether and dried at 0.1 mm over phosphorus pentoxide to give 4.8 g of the sodium salt of the above named cephalosporin derivative; $[\alpha]_D^{23} +109°$ (cl, 75% DMF/pyridine).

$$E_1^1 = 238 \lambda\ 356\ nm\ pH\ 7$$
$$E_1^1 = 162 \lambda\ 262\ nm$$

EXAMPLE 14

N-[6-[4-(N-Acetyl-L-glutaminylamino)phenyl]-1,2-dihydro-2-oxonicotinyl]-7-[D-2-amino-2-phenylacetamido]-3-acetoxymethyl-3-cephem-4-carboxylic acid.

A mixture of 2.15 g (4.9 m mol) of cephaloglycin 2.0 g (4.4 m mol) of Starting Material D and 30 ml of N,N-dimethylacetamide is stirred at 0° and 0.7 ml (4.5 m mol) of the triethylamine is added. The mixture is stirred at 0° for 15 minutes and then at room temperature for 3 hours. The mixture is cooled to 0° and 1.35 ml (4.9 m mol) of 3.6 M sodium 2-ethylhexanoate is added. The solution is poured into 175 ml of ethyl acetate and the precipitated solid is filtered, washed with ethyl acetate and ether, and dried. The solid is dissolved in 75 ml of cold water and the pH is adjusted to 2.0 with 12% hydrochloric acid and centrifuged. The solid is resuspended in 40 ml of cold water and dissolved by adjusting the pH to 6.8 with 1 N sodium hydroxide. The solution is clarified by filtration and the filtrate lyophilized to give 3.27 g of the sodium salt of the above named title cephalosporin; $[\alpha]_D^{23} -278°$ (cl, pH 7).

$$E_1^1 = 315 \lambda\ 358\ nm\ pH\ 7$$
$$E_1^1 = 197 \lambda\ 263\ nm$$

EXAMPLE 15

N-[6-[4-(N-Acetyl-L-alanylamino)phenyl]-1,2-dihydro-2-oxonicotinyl]-7-[D-2-amino-2-phenylacetamido]-3-[([5-methyl-1,3,4-thiadiazolyl-2-yl]thio)methyl]-3-cephem-4-carboxylic acid.

A suspension of 2.82 g (4.86 m mol) of 7-[D-2-amino-2-phenylacetamido]-3-[([5-methyl-1,3,4-thiadiazolyl-2-yl]thio)methyl]-3-cephem-4-carboxylic acid trifluoroacetic acid salt [J. Antibiot., 29, 65 (1976)], 1.91 g (4.86 m mol) of Starting Material I, 20 ml of N,N-dimethylacetamide and 20 ml of DMSO is stirred at room temperature and 1.5 ml (4.95 m mol) of 3.3 M sodium-2-ethylhexanoate in N,N-dimethylacetamide is added. The reaction is stirred for 2 hrs at room temperature and another 1.5 ml of the sodium 2-ethylhexanoate is added. The dark solution is poured into 400 ml of ethyl acetate and the solid is filtered, washed with ethyl acetate, and dried to give 3.8 g yellow solid. The product is dissolved in 150 ml of ice water and the pH is adjusted to 2.5 with 1 N hydrochloric acid. The precipitate is filtered, washed with ice water and resuspended in 100 ml of water. The pH is adjusted to 7.5 with 1 N sodium hydroxide and the solution is lyophilized to give 3.2 g of the sodium salt of the title compound: $[\alpha]_D^{23} -42.5°$ (cl, 75% DMF/pyridine).

$$E_1^1 = 299 \, \lambda \text{ max } 358 \text{ nm} \\ E_1^1 = 225 \, \lambda \quad 268 \text{ nm} \text{ pH } 7$$

EXAMPLE 16

N-[6-[4-(L-Pyroglutamylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A suspension of 3.72 g (6 m mol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 25 ml of N,N-dimethylacetamide is stirred at room temperature and 2.15 g (5.5 m mol) of Starting Material L is added followed by 1.0 ml (7.2 m mol) of triethylamine. The resulting solution is stirred at room temperature for 3.5 hrs. and 1.5 ml (10.8 m mol) of triethylamine is added. The reaction mixture is added dropwise to 250 ml of ethyl acetate. The precipitate is filtered, washed with ethyl acetate and ether and dried. The crude salt is dissolved in 200 ml of ice water and is precipitated by adjusting the pH to 2.0 with 1 N hydrochloric acid. The solid is suspended in 100 ml of 0.01 N hydrochloric acid and the pH adjusted to 2.2 and the solid is filtered and washed with 0.01 N hydrochloric acid. The wet filter cake is suspended in 100 ml of water and dissolved by adjusting the pH to 6.8 with 1 N sodium hydroxide. Lyophilization gives 4.5 g of the disodium salt. The salt is purified by chromatography on Sephadex G-10 with water as the elution solvent. The best fractions are combined and lyophilized to give 2.67 g of the disodium salt of the title cephalosporin derivative; $[\alpha]_D^{23} -98°$ (cl, pH 7).

$$E_1^1 = 319 \, \lambda \, 358 \text{ nm} \\ E_1^1 = 239 \, \lambda \, 266 \text{ nm} \text{ pH } 7$$

EXAMPLE 17

N-[6-[4-(N-Acetyl-DL-prolylamino)phenyl]-1,2-dihydro-2-oxonicotinyl]-7-[D-2-amino-2-phenylacetamido]-3-acetoxymethyl-3-cephem-4-carboxylic acid.

A suspension of 3.23 g (7.9 m mol) of cephaloglycin and 35 ml of N,N-dimethylacetamide is stirred at 0°-5° and 3.01 g (7.2 m mol) of Starting Material F is added followed by 1.05 ml (7.5 m mol) of triethylamine. The reaction is stirred at room temperature for 4 hrs, filtered, and the filtrate poured into 300 ml of ice water containing 10 ml of 1 N hydrochloric acid. The pH is adjusted to 2.6 with 1 N hydrochloric acid and the solids filtered. The product is suspended in water and the pH adjusted to 6.8 with 1 N sodium hydroxide. The resulting solution is lyophilized to give 4.47 g of product. This material is dissolved in 250 ml of water and the pH lowered to 2.5 with 1 N hydrochloric acid. The mixture is shaken with ethyl acetate and the solid is filtered, resuspended in 200 ml of water and the pH adjusted to 6.6 with 1 N sodium hydroxide. The solution is clarified by filtration and lyophilized to give 3.2 g of the sodium salt of the title cephalosporin; $[\alpha]_D^{23} +57°$ (cl, 75% DMF/pyridine).

$$E_1^1 = 371 \, \lambda \, 358 \text{ nm} \\ E_1^1 = 263 \, \lambda \, 235 \text{ nm} \text{ pH } 7$$

EXAMPLE 18

N-[6-[4-(N-Acetyl-DL-alanylamino)phenyl]-1,2-dihydro-3-oxonicotinyl]-7-[D-2-amino-2-phenylacetamido]-3-[[(1-methyl-1H-tetrazol-5-yl)thio]methyl]-3-cephem-4-carboxylic acid.

A mixture of 2.82 g (6 m mol) of 7-[D-2-amino-2-phenylacetamido]-3-[[(1-methyl-1H-tetrazol-5-yl)thio]methyl]-3-cephem-4-carboxylic acid [J. Antibiot., 29, 65 (1976)], 2.36 g (6 m mol) of Starting Material H, 25 ml of N,N-dimethylacetamide, and 10 ml of DMSO is stirred at room temperature and 1.82 ml (6 m mol) of 3.3 M sodium 2-ethylhexanoate is added. The reaction mixture is stirred at room temperature for 3 hrs and filtered. The filtrate is poured into 350 ml of ethyl acetate and the precipitate is filtered. The solids are dissolved in 300 ml of cold water, the pH is adjusted to 2.0 and the free acid collected. The product is slurried in 150 ml of cold water and the pH is brought to 7.6 with 1 N sodium hydroxide, filtered, and the filtrate lyophilized to give 3.3 g of the sodium salt of the above named cephalosporin; $[\alpha]_D^{23} -242°$ (cl, pH 7)

$$E_1^1 = 350 \, \lambda \, 355 \text{ nm} \\ E_1^1 = 205 \, \lambda \, 265 \text{ nm} \text{ pH } 7$$

EXAMPLE 19

N-[6-[4-(N-Acetyl-D-alanylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid.

The D-alanyl compound is made by the method for Example 18 using the imidazolide of 6-[4-(N-acetyl-D-alanyl)aminophenyl]-1,2-dihydro-2-oxonicotinic acid, (Starting Material B). The compound is isolated as the sodium salt of the above named cephalosporin; $[\alpha]_D^{23} -280°$ (cl, pH 7).

$$E_1^1 = 299 \, \lambda \, 358 \text{ nm} \\ E_1^1 = 198 \, \lambda \, 265 \text{ nm} \text{ pH } 7$$

EXAMPLE 20

N-[6-[4-(N-Acetyl-L-alanylamino)phenyl]-1,2-dihydro-2-oxonicotinyl]7-[D-2-amino-2-phenylacetamido]-3-[[(1-methyl-1H-tetrazol-5-yl)thio]methyl]-3-cephem-4-carboxylic acid.

The L-alanyl compound is prepared by the method of Example 18 using the imidazolide of 6-[4-(N-acetyl-L-alanyl)aminophenyl]-1,2-dihydro-2-oxonicotinic acid, (Starting Material I). The compound is isolated as the sodium salt of the above named cephalosporin; $[\alpha]_D^{23} -147°$ (cl, pH 7).

$$E_1^1 = 321 \, \lambda \, 358 \text{ nm} \\ E_1^1 = 220 \, \lambda \, 265 \text{ nm} \text{ pH } 7$$

EXAMPLE 21

N-[6-[4-(N-Acetyl-L-glutaminylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A suspension of 3.7 g (6 m mol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979 r (1977)], 2.3 g (5 m mol) of Starting Material D and 25 ml of N,N-dimethylacetamide is stirred at room temperature for 3 hrs and 2.5 ml (18 m mol) of triethylamine is added over a 10 min period. The resulting solution is stirred for an additional 2 hrs and then is poured into 300 ml of ethyl acetate. The precipitate triethylamine salt is collected, dissolved in 450 ml of cold water, and the pH adjusted to 2.1 with 1 N hydrochloric acid. The precipitate is collected, slurried in 150 ml of cold water and the pH is brought to 6.9 with 1 N sodium hydroxide, and filtered. The filtrate is lyophilized to give 3.9 g of crude product. The material is dissolved in 20 ml of cold water and 45 ml of acetone is added. The precipitate is discarded and the solution is further diluted with 150 ml of acetone. This precipitate is collected, dissolved in 100 ml of water and lyophilized to give 2.3 g of the disodium salt of the above named final product; $[\alpha]_D^{23} -205°$ (cl, pH 7).

$$E_1^1 = 294 \; \lambda \; 360 \text{ nm} \atop E_1^1 = 203 \; \lambda \; 266 \text{ nm} \text{ pH 7}$$

EXAMPLE 22

N-[6-[4-(N-Acetyl-DL-alanylamino)phenyl]-1,2-dihydro-2-oxonicotinyl]-7-[D-2-amino-2-phenylacetamido]-3-[([4-methyl-1,3,4-thiadiazol-2-yl]thio)methyl]-3-cephem-4-carboxylic acid.

A solution of 2.90 g (5 m mol) of 7-[D-2-amino-2-phenylacetamido]-3-[([5-methyl-1,3,4-thiadiazolyl-2-yl]thio)methyl]-3-cephem-4-carboxylic acid trifluoroacetic acid salt [J. Antibiot., 29, 65 (1976)] and 20 ml of N,N-dimethylacetamide is stirred at room temperature and 2.0 g (5.1 m mol) of Starting Material H is added followed by 1.6 ml (5.3 m mol) of 3.3 M sodium-2-ethylhexanoate in N,N-dimethylacetamide and 20 ml of DMSO. The reaction is stirred at room temperature for 2.5 hrs and 1.5 ml (4.95 m mol) of 3.3 M sodium-2-ethylhexanoate in N,N-dimethylacetamide is added and stirring continued for another hour. The reaction solution is poured into 500 ml of ethyl acetate and the precipitate filtered washed with ethyl acetate and dried. The solids are dissolved in 200 ml of water and the solution is acidified with 1 N hydrochloric acid. The solid free acid is filtered washed with water and resuspended in 150 ml of water. The pH is adjusted to 7.0 with 1 N sodium hydroxide and the solution is lyophilized to give 3.5 g of the sodium salt of the above named cephalosporin; $[\alpha]_D^{23} -251°$ (cl, pH 7).

$$E_1^1 = 323 \; \lambda \; 358 \text{ nm} \atop E_1^1 = 216 \; \lambda \; 269 \text{ nm} \text{ pH 7}$$

EXAMPLE 23

N-[6-[4-(N-Acetyl-D-asparaginylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid.

Using the method for Example 18, 2.82 g of 7-[D-2-amino-2-phenylacetamido]-3-[[(1-methyl-1H-tetrazol-5-yl)thio]methyl]-3-cephem-4-carboxylic acid [J. Antibiot., 29, 65 (1976)], 2.62 g (6 m mol) of Starting Material G, 15 ml of N,N-dimethylacetamide and 15 ml of DMSO are allowed to react at room temperature for 2.5 hrs. Work up and lyophilization of a pH 8.0 solution gives 3.8 g of the lithium salt of the above named cephalosporin; $[\alpha]_D^{23} +34°$ (cl, 75% DMF/pyridine).

$$E_1^1 = 311 \; \lambda \; 358 \text{ nm} \atop E_1^1 = 218 \; \lambda \; 266 \text{ nm} \text{ pH 7}$$

EXAMPLE 24

N-[6-[4(N-Acetyl-D-alanylamino)phenyl]-1,2-dihydro-2-oxonicotinyl]-7-[D-2-amino-phenylacetamido]-3-carbamoyloxymethyl-3-cephem-4-carboxylic acid.

A solution of 1.50 g (2.88 m mol) of 7-[D-2-amino-2-phenylacetamido]-3-carbamoyloxymethyl-3-cephem-4-carboxylic acid trifluoroacetic acid salt, [Belgium Pat. No. 835,238] 0.87 ml 2.87 m mol) of 3.3 M sodium-2-ethylhexanoate in N,N-dimethylacetamide and 15 ml of N,N-dimethylacetamide is stirred at room temperature and 1.13 g (2.88 m mol) of Starting Material B is added. The reaction is stirred at room temperature for 2.5 hrs and 0.87 ml (2.87 m mol) of 3.3 M sodium 2-ethylhexanoate in N,N-dimethylacetamide is added. The solution is added dropwise to 100 ml of ethyl acetate and the solids filtered, washed with ethyl acetate, and dried. The precipitate is dissolved in 100 ml of cold water and the pH adjusted to 2.5 with 1 N hydrochloric acid. The solid is filtered, washed with water and resuspended in 100 ml of cold water and the pH is adjusted to 7.5 with 1 N sodium hydroxide. Filtration and lyophilization gives 1.8 g of the sodium salt of the title compound; $[\alpha]_D^{23} -475°$ (cl, pH 7).

$$E_1^1 = 373 \; \lambda \; 358 \text{ nm} \atop E_1^1 = 232 \; \lambda \; 261 \text{ nm} \text{ pH 7}$$

EXAMPLE 25

N-[6-[4(N-Acetyl-D-alanylamino)phenyl]-1,2-dihydro-2-oxonicotinyl]-7-[D-2-amino-2-(4-hydroxyphenyl)acetamido]-3-[[(1-methyl-1H-tetrazol-5-yl)thio]methyl]-3-cephem-4-carboxylic acid.

A suspension of 1.79 g (4.55 m mol) of Starting Material B, 10 ml of N,N-dimethylacetamide and 10 ml of DMSO is stirred at room temperature and 2.60 g (5.46 m mol) of 7-[D-2-amino-2-(4-hydroxyphenyl)acetamido]-3-[[(1-methyl-1H-tetrazol-5-yl)thio]methyl]-3-cephem-4-carboxylic acid [J. Antibiot., 29, 65 (1976)] is added. The reaction mixture is stirred for 4 hrs at room temperature and 2 ml (6.54 m mol) of 3.27 M sodium 2-ethylhexanoate in N,N-dimethylacetamide is added. The solution is then added dropwise to 200 ml of rapidly stirred ethyl acetate. The precipitate is filtered, washed with ethyl acetate, and dried to give 4.47 g crude product. The solids are dissolved in 150 ml of ice water and the pH is adjusted to 2.0 with 1 N hydrochloric acid. The precipitate is centrifuged, washed with water and centrifuged. The solids are suspended in 150 ml of ice water and are brought into solution by adjusting the pH to 7.5 with 1 N sodium hydroxide. The solution is lyophilized to give 3.30 g yellow solid. The compound is further purified using preparative high pressure liquid chromatography on a C-18 reverse phase column using 80:20 water acetonitrile as elution solvent. Lyophilization of the appropriate fractions gives 1.95 g of the sodium salt of the above named final product; $[\alpha]_D^{23} +24°$ (c 0.5, 50% MeOH/pH 7.

$$E_1^1 = 350 \ \lambda \ 358 \text{ nm} \atop = 236 \ \lambda \ 268 \text{ nm} \text{ pH 7}$$

EXAMPLE 26

N-[6-[4-(N,N'-Diacetyl-DL-lysylamino)phenyl]-1,2-dihydro-2-oxonicotinyl]-7-[D-2-amino-2-phenylacetamido]3-[[(1-methyl-1H-tetrazol-5-yl)thio]-methyl]-3-cephem-4-carboxylic acid.

A mixture of 3.40 g (6 m mol) of 7-[D-2-amino-2-phenylacetamido]-3-[[(1-methyl-1H-tetrazol-5-yl)thio]-methyl]-3-cephem-4-carboxylic acid [J. Antibiot., 29, 65 (1976)], 2.96 g (6 m mol) of Starting Material M and 50 ml of N,N-dimethylacetamide is stirred at room temperature for 4 hrs. The reaction is filtered and the filtrate poured into 250 ml of ice water. The pH is adjusted to b 2.0 with 0.1 N hydrochloric acid and the solids filtered and washed with water. The product is resuspended in 75 ml of water and the pH adjusted to 6.5 with 0.1 N sodium hydroxide. Filtration and lyophilization gives 4.9 g of the sodium salt of the title cephalosporin derivative; $[\alpha]_D^{23} +83°$ (c1, pH 7).

$$E_1^1 = 279 \ \lambda \ 358 \text{ nm} \atop = 185 \ \lambda \ 263 \text{ nm} \text{ pH 7}$$

EXAMPLE 27

N-[6-[4-(N,N'-Diacetyl-DL-lysylamino)phenyl]-1,2-dihydro-2-oxonicotinyl]-7-[D-2-amino-2-phenylacetamido]-3-acetoxymethyl-3-cephem-4-carboxylic acid.

A suspension of 2.2 g (4.5 m mol) of Starting Material M and 50 ml of N,N-dimethylacetamide is stirred at 10° and 2.0 g (4.5 m mol) of cephaloglycin is added. Stirring is continued at room temperature for 4 hrs and 0.63 ml (4.5 m mol) of triethylamine is added. After an additional hour, the reaction mixture is filtered and the filtrate poured onto 150 g of crushed ice. The pH is adjusted to 2.0 with 0.1 N hydrochloric acid and the solid is and washed with cold water. The solids are resuspended in ice water and the pH adjusted to 6.5 with 0.1 N sodium hydroxide. Lyophilization gives 2.9 g of the sodium salt of the above named final product; $[\alpha]_D^{23} -64°$ (c1, pH 7); $[\alpha]_D^{23} +97.5°$ (c1, DMSO);

$$E_1^1 = 345 \ \lambda \ 358 \text{ nm} \atop = 211 \ \lambda \ 263 \text{ nm} \text{ pH 7}$$

EXAMPLE 28

N-[6-[3-(N-Acetyl-D-alanylaminophenyl]-1,2-dihydro-2-oxonicotinyl]-7-[D-2-amino-2-phenylacetamido]-3-acetoxymethyl-3-cephem-4-carboxylic acid.

A suspension of 3.24 g (8.0 m mol) of cephaloglycin and 50 ml of N,N-dimethylacetamide is stirred at room temperature and 3.0 g (7.6 m mol) of Starting Material J is added. The reaction mixture is stirred at room temperature for 4 hrs and added dropwise to 450 ml of stirring ethyl acetate. The precipitate is filtered, washed with ethyl acetate, 1:1 ethyl acetate ether, and dried. The solids are dissolved in water and the pH is adjusted to 2.5 with 1 N hydrochloric acid. The solid is filtered washed with ice water, and suspended in 200 ml of ice water. The pH is adjusted to 7.0 with 1 N sodium hydroxide and the solution is clarified by filtration. Lyophilization of the filtrate gives 3.0 g of the sodium salt of the appropriate cephalosporin compound; $[\alpha]_D^{23} -3.9°$ (c1, pH 7);

$$E_1^1 = 304 \ \lambda \ 349 \text{ nm} \atop = 390 \ \lambda \ 243 \text{ nm} \text{ pH 7}$$

EXAMPLE 29

N-[6-[4-(D-Alanylamino)phenyl]-1,2-dihydro-2-oxonicotinyl]-7-[D-2-amino-2-phenylacetamido]-3-acetoxymethyl-3-cephem-4-carboxylic acid.

A suspension of 1.87 g (4.6 m mol) of cephaloglycin, 15 ml of N,N-dimethylacetamide, and 15 ml of DMSO is stirred at 5° and 2.0 g (4.45 m mol) of Starting Material k is added. The reaction is stirred at 5° for 1 hr and then at room temperature for 2.5 hrs. The reaction mixture is poured into 100 ml of ice water and filtered. The pH of the filtrate is adjusted from 6.8 to 4.0 with 1 N hydrochloric acid. The product is separated by filtration, washed with water and resuspended in 100 ml of ice water. Adjustment of the pH to 5.5 with 1 N ammonium hydroxide and lyophilization gives 2.25 g of the above named cephalosporin;

$$E_1^1 = 302 \ \lambda \ 356 \text{ nm} \atop = 223 \ \lambda \ 263 \text{ nm} \text{ pH 7}$$

EXAMPLE 30

N-[6-[4-(N-Acetyl-4-hydroxy-L-prolylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A solution of 4.02 g (6.5 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 20 ml of dried N,N-dimethylacetamide is stirred at 0°–5° and 2.2 ml (15.78 mmol) of triethylamine is added. The solution is stirred for 5 min in an ice bath, and 2.80 g (5.52 mmol) of Starting Material S is added. The mixture is stirred for 4 hrs at 0°–5° and 0.4 ml (2.86 mmol) of triethylamine is added. The resulting solution is poured into 320 ml of cold ethyl acetate with stirring. After stirring for another 20 min, the mixture is filtered, the solid is washed with cold ethyl acetate, then with 50 ml cold, anhydrous ether, and dried 15 min under vacuum to give 7.69 g of solid. The solid is dissolved in 80 ml of stirred cold water, and the pH is adjusted to 2.4 with 0.2 N hydrochloric acid during 1.5 hours, and the product is precipitated in the acid form. It is separated by centrifugation at 0° at 9000 rpm, washed with 55 ml of 0.0032 N hydrochloric acid, then two times with 80 ml portions of cold water, then suspended in 40 ml cold water. The solid is dissolved by adjusting the pH to 6 with cold 0.15 N sodium hydroxide. The resulting solution is lyophilized to give 4.26 g of the title cephalosporin as the sodium salt; $[\alpha]_D^{23} -258°$ (c1, pH 7).

EXAMPLE 31

N-[6-[4-(N-Acetyl-4-hydroxy-L-prolylamino)phenyl]-1,2-dihydro-2-oxonicotinyl]-7-[D-2-amino-2-phenylacetamido]-3-acetoxymethyl-3-cephem-4-carboxylic acid.

A solution of 2.489 g (4.90 mmol) of Starting Material S, 0.65 ml of 2-methoxypropane, and 15 ml of N,N-dimethylacetamide is stirred in an ice bath and 0.8 ml (5.74 mmol) of triethylamine is added followed by 2.38 g (5.81 mmol) of cephaloglycin and 0.75 ml of dimethyl sulfoxide. The mixture is stirred for 8 hrs at 0°, kept at −28° for 9 hrs, then stirred for 2.5 hrs at 0°. The mixture is filtered and the filtrate is dropped into 300 ml of stirred, ice cold ethyl acetate, followed by 200 ml of cold ether. After stirring at 0°, the mixture is filtered and the solid is washed with 500 ml of cold ethyl acetate and ether, then with 50 ml of ether and dried to give 4.42 g of solid. This solid is combined with 0.30 g from another run and dissolved in 75 ml of cold water. The pH is adjusted to 2.5 with 0.3 N hydrochloric acid. The mixture is centrifuged at 9000 rpm at 0°, decanted, and the solid is washed with 50, 25, and 5 ml portions of water. The solid is suspended in 25 ml of cold water and brought into solution by adjusting the pH to 6.7 with 0.25 N sodium hydroxide. The resulting solution is lyophilized to give 3.42 g of the title cephalosporin sodium salt; $[\alpha]_D^{23} -276°$, (c0.53, pH 7).

EXAMPLE 32

N-[6-[4-[N-Acetyl-4-(acetyloxy)-L-prolylamino]-phenyl]-1,2-dihydro-2-oxoniotinyl]-7-[D-2-amino-2-phenylacetamido]-3-acetoxymethyl-3-cephem-4-carboxylic acid.

A suspension of 2.64 g (6.0 mmol) of cephaloglycin and 50 ml of N,N-dimethylacetamide is stirred at 0°–5° and 2.6 g (5.5 mmol) of Starting Material N is added followed by 0.7 ml (5.0 mmol) of triethylamine. The mixture is stirred at 0°–5° for 30 min, then at room temperature for 4 hrs. Insoluble material is filtered off and 2.0 ml (6.7 mmol) of 3.2 M sodium 2-ethylhexanoate in N,N-dimethylacetamide is added to the filtrate. The resulting solution is added to 800 ml of ethyl acetate and the precipitated solid is filtered off and dried. The solid is dissolved in 200 ml of ice water and acidified to pH 2.0 with hydrochloric acid. The precipitated solid is filtered and suspended in 200 ml of ice water and stirred for 20 min and filtered. The solid is resuspended in 100 ml of ice water and the pH is adjusted to 6.5 with 1 N sodium hydroxide and the solution is lyophilized to give 3.29 g of the title cephalosporin as the sodium salt; $[\alpha]_D^{23} -178°$ (c1, pH 7).

$$E_1^1 = 341 \ \lambda \ 358 \text{ nm} \atop E_1^1 = 207 \ \lambda \ 263 \text{ nm} \text{ pH 7}$$

EXAMPLE 33

N-[6-[4-[N-Acetyl-4-(formyloxy)-L-prolylamino]-phenyl]-1,2-dihydro-2-oxonicotinyl]-7-[D-2-amino-2-phenylacetamido]-3-acetoxymethyl-3-cephem-4-carboxylic acid.

A mixture of 4.9 g (11 mmol) of cephaloglycin and 3.58 g (10 mmol) of Starting Material O in 100 ml of a 1:1 mixture of N,N-dimethylacetamide and dimethyl sulfoxide is stirred at room temperature for 5 hrs. The mixture is filtered and the filtrate is treated with 3.0 ml (10 mmol) of 3.2 M sodium 2-ethylhexanoate in N,N-dimethylacetamide and the resulting solution is added to 500 ml of ethyl acetate and 400 ml of ethyl ether. The precipitated solid is filtered, washed with ethyl ether and dried. The solid is dissolved in 400 ml of ice water, the pH is adjusted to 3.0 with hydrochloric acid, the precipitated solid is filtered and washed with water. The solid is suspended in 200 ml of ice water and the pH is adjusted to 6.5 with 1 N sodium hydroxide. The solution is lyophilized to give 3.65 g of solid, which is purified by preparative HPLC using a C-18 reverse phase column and a 80:20 mixture of acetonitrile and water as eluent to give 1.2 of the title cephalosporin as the sodium salt; $[\alpha]_D^{23} -191°$ (c1, pH 7).

$$E_1^1 = 355 \ \lambda \ 358 \text{ nm} \atop E_1^1 = 215 \ \lambda \ 264 \text{ nm} \text{ pH 7}$$

EXAMPLE 34

N-[6-[4-[N-Methyl-5-oxo-L-prolylamino]phenyl]-1,2-dihydro-2-oxo-nicotinyl]-7-[D-2-amino-2-phenylacetamido]-3-acetoxymethyl-3-cephem-4-carboxylic acid.

A mixture of 2.0 g (4.6 mmol) of cephaloglycin and 1.9 g (4.2 mmol) of Starting Material Q in 40 ml of 1:1 mixture of N,N-dimethylacetamide and dimethyl sulfoxide is stirred at room temperature for 5 hrs. The mixture is filtered and 1.8 ml (60 mmol) of 3.2 M sodium 2-ethylhexanoate in N,N-dimethylacetamide is added to the filtrate and the resulting solution is added to 500 ml of ethyl acetate and 400 ml of ethyl ether. The precipitated solid is filtered off, washed with ethyl ether, and dried. The solid is dissolved in 200 ml of ice water and acidified to pH 2.5 with hydrochloric acid. The solid is filtered and suspended in 200 ml of ice water for 20 min. The suspension is filtered and the solid is resuspended in 100 ml of ice water and the pH is adjusted to 6.5 with 1 N sodium hydroxide and the solution is lyophilized to give 2.7 g of the title cephalosporin as the sodium salt; $[\alpha]_D^{23} +22.6°$ (c1, pH 7).

$$E_1^1 = 396 \ \lambda \ 358 \text{ nm} \atop E_1^1 = 242 \ \lambda \ 262 \text{ nm} \text{ pH 7}$$

EXAMPLE 35

N-[6-[4-(N,N'-Diacetyl-L-lysylamino)phenyl]-1,2-dihydro-2-oxonicotinyl]-7-[D-2-amino-2-phenylacetamido]-3-acetoxymethyl-3-cephem-4-carboxylic acid.

A suspension of 1.7 g (3.5 mmol) of Starting Material R and 1.7 g (3.85 mmol) of cephaloglycin in 40 ml of dry N,N-dimethylacetamide is stirred for 5 hrs at room temperature and filtered. The filtrate is cooled to 0° and treated with 1.3 ml (4.68 mmol) of 3.6 M sodium 2-ethylhexanoate in N,N-dimethylacetamide for 10 min and 100 ml of ethyl acetate is added in portions over a period of 15 min. The resulting precipitate is collected, washed with ethyl acetate and ether. The solid is suspended in 150 ml of ice water and acidified with 1 N hydrochloric acid to pH 2.0, stirred for 15 min and filtered. It is again stirred with 100 ml of water at 1° for 10 min, filtered, and washed until washings become neutral. At this point the solid is suspended in 50 ml of ice cold water and the pH is adjusted to 6.5 with 0.1 N sodium hydroxide. The solution is filtered and the filtrate is lyophilized to give 2.4 g of title cephalosporin as the sodium salt; $[\alpha]_D^{23}+18.0°$ (cl, pH 7).

$$E_1^1 = 194 \lambda\ 262\ nm \atop 308 \lambda\ 358\ nm\ pH\ 7$$

EXAMPLE 36

N-[6-[4-[N-Acetyl-4-(1-oxopropoxy)-L-prolylamino]-phenyl]-1,2-dihydro-2-oxonicotinyl]-7-[D-2-amino-phenylacetamido]-3-[[(1-carboxymethyl-1H-tetrazol-5-yl)thio]methyl]-3-cephem-4-carboxylic acid.

A solution of 3.72 g (6 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 25 ml of N,N-dimethylacetamide is stirred at 0°–5° C. and 1.7 ml (12 mmol) of triethylamine is added in portions, followed by 2.7 g (5.5 mmol) of Starting Material P. The mixture is stirred at 0°–5° for 1 hr and then at room temperature for 2 hrs and 0.84 ml (6 mmol) of triethylamine is added. The solution is poured into 300 ml of ethyl acetate with stirring and the precipitate is collected and washed with ethyl acetate. the filtercake is dissolved in 300 ml water at 0°–5° and the pH is lowered to 2.2 with hydrochloric acid. The precipitated acid is collected and washed with water of pH 2. The filtercake is then resuspended in 150 ml water at 0°–5° and the pH is adjusted to 7.5 with 1 N sodium hydroxide solution. The solution is filtered and the filtrate is lyophilized, leaving 5.0 g of the title cephalosporin as disodium salt; $[\alpha]_D^{23}-154°$ (cl, pH 7).

$$E_1^1 = 276 \lambda\ 360\ nm \atop 188 \lambda\ 267\ nm\ pH\ 7$$

EXAMPLE 37

N-[6-[4-(N-Acetyl-D-glutaminylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A suspension of 3.1 g (5 mmol) of 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979r (1977)] and 25 ml of N,N-dimethylacetamide is stirred at 0°–5° and 1.4 ml (10 mmol) of triethylamine is added in portions, followed by 1.8 g (4 mmol) of Starting Material T. The mixture is stirred at 0°–5° for 30 min then at room temperature for 3 hrs and 0.7 ml (4 mmol) triethylamine is added. The solution is poured into 300 ml ethyl acetate, the precipitate is collected and washed with ethyl acetate. The filtrate is dissolved in 300 ml water at 0°–5° and the pH is brought to 2.2 with dilute hydrochloric acid. The precipitate is collected and washed with cold water of pH 2. The resulting filtercake is resuspended in 150 ml water at 0°–5° and the pH is adjusted to 7.0 with dilute sodium hydroxide solution. The solution is filtered and the filtrate is freeze dried, leaving 3.7 g of the title cephalosporin as the disodium salt; $[\alpha]_D^{23}-141°$ (cl, pH 7).

$$E_1^1 = 308 \lambda\ 360\ nm \atop 215 \lambda\ 267\ nm\ pH\ 7$$

EXAMPLE 38

N-[6-[4-(L-Glutaminylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid.

A solution of 2.73 g (4.4 mmol) 7-[D-2-amino-2-phenylacetamido]-3-[[(1-carboxymethyl-1H-tetrazol-5-yl)thio]methyl]-3-cephem-4-carboxylic acid trifluoroacetic acid salt [Chem. Abstr., 86, 189979 (1977)], 2.0 g (3.9 mmol) of Starting Material U, and 40 ml of N,N-dimethylacetamide is stirred at 0°–5° and 2.75 ml (8.8 mmol) of 3.2 M sodium 2-ethylhexanoate in N,N-dimethylacetamide is slowly added. The reaction is stirred at 5° for 2 hr and room temperature for 2.5 hrs, and 1.38 ml (4.4 mmol) of 3.2 M sodium 2-ethylhexanoate in N,N-dimethylacetamide is added. The solution is poured into 450 ml of rapidly stirring ethyl acetate. The resulting precipitate is stirred until grannular, filtered, washed with ethyl acetate, resuspended in ethyl acetate and stirred until a fine powder results. The solid is filtered, washed with ether and dried. The dry powder is added in portions to a solution of 15 ml of anisole in 45 ml of trifluoroacetic acid. The solution is stirred at 0°–5° for 1 hr and the solvent is removed under reduced pressure. The residue is triturated with ether until a grannular precipitate develops. The solid is filtered, washed with ether, resuspended in ether and stirred until a fine powder forms. The precipitate is filtered, washed with ether, and dried. The solid is dissolved in ice water and the pH is adjusted to 1.8 with hydrochloric acid and centrifuged. The centrifugate is resuspended at 5° in pH 1.8 water and centrifuged. The solid is dissolved in ice water by adjusting the pH to 6.8 with 1 N sodium hydroxide. The solution is clarified by filtration and the filtrate lyophilized to give 3.0 g of the title cephalosporin as the sodium salt; $[\alpha]_D^{23}+76°$ (cl, pH 7).

$$E_1^1 = 275 \lambda\ 358\ nm \atop 194 \lambda\ 267\ nm\ pH\ 7$$

EXAMPLE 39

N-[6-[4-[N-Acetyl-4-(1-oxopropoxy)-L-prolylamino]-phenyl]-1,2-dihydro-2-oxonicotinyl]-7-[D-2-amino-2-phenylacetamido]-3-acetoxymethyl-3-cephem-4-carboxylic acid.

A suspension of 3.53 g (8 mmol) of cephaloglycin dihydrate and 35 ml of N,N-dimethylacetamide is stirred at 0°–5° and 3.94 g (8 mmol) of Starting Material P is added followed by 1.12 ml (8 mmol) of triethylamine. The reaction is stirred at 0°–5° for 30 min and at room temperature for 4 hrs. The reaction mixture is cooled and 3.3 ml (12 mmol) of 3.6 M sodium 2-ethylhexanoate in N,N-dimethylacetamide is added. After 15 min the resulting solution is poured into rapidly stirring cold ethyl acetate. The precipitated solid is filtered, washed with cold ethyl acetate, ether, and dried. The solid is dissolved in water and the pH is adjusted to 2 with dilute hydrochloric acid. The solid is filtered and washed with cold water and suspended in cold water. The pH is adjusted to 6 with dilute sodium hydroxide. The solution is clarified by filtration and the filtrate lyophilized to give 5.0 g of the title cephalosporin as the sodium salt; $[\alpha]_D^{23} -121°$ (cl, pH 7).

$$E_1^1 = \frac{333 \lambda 358 \text{ nm}}{204 \lambda 263 \text{ nm}} \text{ pH 7}$$

EXAMPLE 40

N-[6-[4-[N-Acetyl-4-(1-oxopropoxy)-L-prolylamino]-phenyl]-1,2-dihydro-2-oxonicotinyl]-7-[D-2-amino-2-ohenylacetamido]-3-[[(1-methyl-1H-tetrazol-5-yl)thio]-methyl]-3-cephem-4-carboxylic acid.

A solution of 1.44 g (2.5 mmol) of 7-[D-2-amino-2-phenylacetamido]-3-[[(1-methyl-1H-tetrazol-5-yl)thio]-methyl]-3-cephem-4-carboxylic acid trifluoroacetic acid salt [J. Antibiot., 29, 65 (1976)] and 20 ml of N,N-dimethylacetamide is stirred at room temperature and 1.23 g (2.5 mmol) of Starting Material P is added. The solution is cooled in an ice bath and 0.35 ml (25 mmol) of triethylamine is added. The ice bath is removed and the reaction is stirred at room temperature for 4 hrs and 1.04 ml (3.75 mmol) of 3.6 M sodium 2-ethylhexanoate in N,N-dimethylacetamide is added. The resulting solution is poured into rapidly stirring ethyl acetate and the precipitated solid is filtered, washed with ethyl acetate and ether, and dried. The solid is dissolved in water and the pH is adjusted to 2 with dilute hydrochloric acid. The solid is filtered, washed with water, and resuspended in water. The pH is adjusted to 6 with dilute sodium hydroxide and the solution is lyophilized to give 1.11 g of the title cephalosporin as the sodium salt; $[\alpha]_D^{23} -67°$ (cl, pH 7).

$$E_1^1 = \frac{317 \lambda 359 \text{ nm}}{213 \lambda 266 \text{ nm}} \text{ pH 7}$$

EXAMPLE 41

N-[6-[4-(N-Acetyl-D-alanylamino)phenyl]-1,2-dihydro-2-oxonicotinyl]-7-[D-2-amino-2-phenylacetamido]-3-[[[(1-(2-carboxyethyl)-1H-tetrazol-5-yl]-thio]methyl]-3-cephem-4-carboxylic acid.

A suspension of 31 g (80 mmol) of 7-amino-3-[[[1-(2-carboxyethyl)-1H-tetrazol-5-yl]thio]methyl]-3-cephem-4-carboxylic acid [Belgium Pat. No. 856,637], 150 ml of tetrahydrofuran and 200 ml of water is stirred at 0°-5° and 22.4 ml (160 mmol) of triethylamine is added in portions to give a solution, which is kept at −5°. The mixed anhydride of t-butoxycarbonyl phenylglycine is formed in a separate flask as follows. A mixture of 30.2 g (120 mmol) of N-(t-butoxycarbonyl)-D-phenylglycine, 100 ml of tetrahydofuran and 250 ml of acetonitrile is stirred at −10° and 13.2 ml (120 mmol) of N-methylmorpholine is added, followed by 15.6 ml (120 mmol) of isobutyl chlorofomate in a dropwise manner. The reaction mixture is kept at −10° for 15 minutes and the cold solution of the above triethylamine salt is added in one portion to the mixed anhydride. The mixture is stirred at −5° for 1.5 hrs and then at 0°-5° for 16 hrs. The bulk of the solvent is evaporated at reduced pressure and the residue is diluted with 1000 ml of ice water. The pH is adjusted to 2.3 with hydrochloric acid and the product extracted with ethyl acetate. The ethyl acetate extract is evaporated at reduced pressure and the foamy syrup is triturated with 330 ml ether to give 33.9 g of 7-[D-2-t-butoxycarbonylamino-2-phenylacetamido]-3-[[[1-(2-carboxyethyl)-1H-tetrazol-5-yl]thio]methyl-3-cephem-4-carboxylic acid; $[\alpha]_D^{23} -25.4°$, (cl, MeOH, pH 7, 1:1).

$$E_1^1 = 182 \lambda 268 \text{ nm pH 7}$$

A solution of 60 ml of trifluoroacetic acid and 15 ml of 1,3-dimethoxybenzene is stirred at 0°-5° and 12.4 g (20 mmol) of the above protected cephalosporin derivative is added. The solution is stirred at 0°-5° for 30 min and the solvent is removed under reduced pressure. The residue is triturated with 350 ml of ether and the solid is filtered and dried to give 12.16 g of 7-[D-2-amino-2-phenylacetamido]-3-[[[1-(2-carboxyethyl)-1H-tetrazol-5-yl]thio]methyl]-3-cephem-4-carboxylic acid trifluoroacetic acid salt; $[\alpha]_D^{23} -7°$ (cl, MeOH, pH 7, 1:1).

$$E_1^1 = 171 \text{ 267 nm pH 7}$$

A suspension of 3.5 g (5.5 mmol) of the above cephalosporin salt, 2 g (5 mmol) of Starting Material B, and 25 ml of N,N'-dimethylacetamide is stirred at 0°-5° and 1.54 ml (11 mmol) of triethylamine is added. The reaction is stirred at room temperature for 5 hrs and 0.77 ml (5.5 mmol) of triethylamine is added and the solution is poured into 300 ml of ethyl acetate. The precipitated salt is collected and washed with ethyl acetate. The filtercake is dissolved in 280 ml water at 0°-5° and the pH is brought to 2.2 with hydrochloric acid. The precipitated acid is collected, washed with water of pH 2.2 and suspended in 150 ml water at 0°-5° and the pH is adjusted to 7 with 1 N sodium hydroxide solution. The solution is filtered and the filtrate is lyophilized to give 4.05 g of the title cephalosporin as the disodium salt; $[\alpha]_D^{23} -220°$ (cl, pH 7).

$$E_1^1 = \frac{276 \lambda 358 \text{ nm}}{214 \lambda 266 \text{ nm}} \text{ pH 7}$$

EXAMPLE 42

N-[6-[4-(N-Acetyl-L-glutaminylamino)phenyl]-1,2-dihydro-2-oxonicotinyl]-7-[D-2-amino-2-phenylacetamido]-3-[[(1-sulfomethyl-1H-tetrazol-5-yl)thio]methyl]-3-cephem-4-carboxylic acid.

A solution of 1.72 g (2.60 mmol) of 7-[D-2-amino-2-phenylacetamido]-3-[[(1-sulfomethyl-1H-tetrazol-5-yl)thio]methyl-3-cephem-4-carboxylic acid [U.S. Pat. No. 4,048,311] and 7 ml of N,N-dimethylacetamide is stirred at room temperature and 1.17 g (2.6 mmol) of Starting Material D is added followed by 0.81 ml (2.6 mmol) of 3.2 M sodium 2-ethylhexanoate in N,N-dimethylacetamide. The reaction solution is stired at room temperature for 3 hrs and 1.0 ml (3.2 mmol) of 3.2 M sodium 2-ethylhexanoate in N,N-dimethylacetamide is added. After stirring 10 min, the mixture was slowly added to 50 ml of ethyl acetate. The mixture is stirred for 1 hr and the precipitate filtered, washed with ethyl acetate and ether, and dried to give 2.97 g of yellow solid. The solid was dissolved in ice water and the pH is adjusted to 7 with dilute hydrochloric acid. The solution is chromatographed on 250 ml of Sephadex G-10 and the best fractions pooled. Lyophilization affords 2.32 g of the title cephalosporin as the disodium salt; $[\alpha]_D^{23} -177.4°$ (cl, pH 7)

$E_1^1 = 245 \lambda\ 357\ nm$ pH 7
$E_1^1 = 185 \lambda\ 265\ nm$

EXAMPLE 43

N-[2-[4-(N-Acetyl-L-glutaminylamino)phenyl]-1,2-dihydro-2-oxonicotinyl]-7-[D-2-amino-2-(4-hydroxyphenyl)acetamido]-3-[[(1-methyl-1H-tetrazol-5-yl)thio]methyl]-3-cephem-4-carboxylic acid.

A suspension of 6 g (8 mmol) 7-[D-2-amino-2-(4-hydroxyphenyl)acetamido]-3-[[(1-methyl-1H-tetrazol-5-yl)thio]methyl]-3-cephem-4-carboxylic acid (salt with 1.5 eq of p-toluenesulfonic acid) [J. Antibiot., 29, 65 (1976)], 2.93 g (6.5 mmol) of Starting Material D, and 30 ml of N,N-dimethylacetamide is stirred at room temperature and 0.7 ml (5 mmol) of triethylamine is added. The solution is poured into 350 ml of stirring ethyl acetate. The precipitated solid is filtered, washed with ethyl acetate, and dissolved in 400 ml of ice water. The pH is adjusted to 2 with 1N-hydrochloric acid and the precipitate is filtered and washed with cold water of pH 2. The solid is suspended in 200 ml of water at 0°–5° C. and dissolved by adjusting the pH to 7 with 1 N sodium hydroxide. The solution is clarified by filtration and the filtrate lyophilized to give 5.67 g of the title cephalosporin as the sodium salt; $[\alpha]_D^{23} -424°$ (cl, pH 7).

$E_1^1 = 288 \lambda\ 358\ nm$ pH 7
$E_1^1 = 207 \lambda\ 267\ nm$

STARTING MATERIALS

A. A suspension of 330 g (6.1 mol) of sodium methoxide, 3 l of tetrahydrofuran, and 2.5 L of ether is stirred at room temperature and a suspension of 490 g (2.77 mol) of 4-(acetylamino) acetophenone, 416 g (5.54 mol) of ethyl formate, and 3 L of tetrahydrofuran is added over a period of 1 hr. The suspension is stirred at room temperature overnight under nitrogen. The precipitate is allowed to settle and the solvent drawn off with a filter candle. Another 3 L of tetrahydrofuran is added and the solvent again removed by filter candle.

Water (9 L) is added to the residue and the pH is adjusted to 9.0 with glacial acetic acid and 388 g (4.6 mol) of 2-cyanoacetamide is added. The mixture is warmed to 90° on a steam bath while allowing the residual tetrahydrofuran and ether to escape. The system is fitted with a condenser and heated at this temperature overnight. The suspension is cooled and the pH is adjusted to 5.8 with acetic acid. The brown solid is filtered and washed with water, 1:1 methanol water, methanol and finally ethyl acetate. Drying afforded 422 g of 6-(4-acetylaminophenyl)-1,2-dihydro-2-oxonicotinonitrile; m.p.>350°.

A suspension of 422 g (1.67 mol) of the above nitrile and 3650 ml of water containing 932 g of potassium hydroxide is heated at 105° for 40 hrs. The solution is cooled and acidified to pH 4.0 with 1360 ml of concentrated hydrochloric acid and 400 g of potassium hydroxide pellets are added with stirring. After filtration, the pH of the filtrate is adjusted to 4.5 with concentrated hydrochloric acid. The solid is filtered, suspended in 8 L of water and filtered. The solid is washed with methanol and finally ethyl acetate and dried at 60° to give 328 g, m.p. 314°–316° dec.

$E_1^1$ 944 λ 347 nm pH 7.

B. A suspension of 50 g (0.22 mol) of 6-[4-aminophenyl]-1,2-dihydro-2-oxonicotinic acid and 1875 ml of dichloromethane is stirred at room temperature and 91 ml (0.65 mol) of triethylamine is added followed by 85 ml (0.67 mol) of chlorotrimethylsilane. The resulting mixture is stirred at room temperature for 1 hr 45 min.

A stirred solution of 56.9 g (0.44 mol) of acetyl-D-alanine, 1875 ml of dichloromethane, and 48.2 ml (0.44 mol) of N-methylmorpholine is cooled to −15° and 34.6 ml (0.44 mol) of methyl chloroformate is added during a 10 min period and the temperature is allowed to rise to 0° over a 20 min period. The above silylated pyridone acid is then added to the mixed anhydride within 2 min with rapid stirring and ice bath cooling. The reaction mixture is stirred overnight as the ice bath is allowed to melt. The solvent is evaporated and the residue suspended in 1875 ml of water, cooled with an ice bath, and brought into solution by adjusting the pH to 7.5 with 2 N sodium hydroxide. The solution is clarified by filtration and extracted with ether. The aqueous is stirred in an ice bath and the pH adjusted to 2.0 with 3 N hydrochloric acid. The precipitated solid is washed with 1 L of water by centrifugation and isolated by lyophilization of a water slurry. The solid is recrystallized from 320 ml of N,N-dimethylacetamide and 2.3 L of methanol and dried under high vacuum at 55° to give partially dried 84.1 g of 6-[4-(N-Acetyl-D-alanylamino)phenyl]-1,2-dihydro-2-oxonicotinic acid; $[\alpha]_D^{23} +79.5°$ (cl, pH 8), m.p. 298–299d.

A suspension of 78.0 g (0.23 mol) of the above acetyl D-alanyl pyridone acid and 800 ml of the dry DMF is stirred at room temperature and 74.3 g (0.46 mol) of carbonyldiimidazole is added. After 30 min the resulting solution is heated with stirring at 53°–56° for 1 hr 15 min. Approximately 600 ml of DMF is evaporated at bath temperature of 45° with an oil pump and the concentrate is diluted with 900 ml of acetonitrile. The mixture is warmed to ca. 40°, stirred, cooled to room temperature and filtered. The solid is washed with 250 ml of 1:1 acetonitrile ether and ether and dried to give 87 g of yellow solid imidazolide; $[\alpha]_D^{23} +14.4°$ (cl, DMSO).

C. Methyl chloroformate, 1.7 ml (20 m mol), is added to a solution of 2.9 g (20 m mol) of alpha-acetamidoisobutyric acid, 2.2 ml (20 m mol) of N-methylmorpholine in 50 ml of acetonitrile at −15° C. The mixture is stirred at −20° C. to −10° C. for ½ hr and to it is added in a dropwise manner preformed silylated pyridone solution [by stirring a mixture of 2.3 g of the p-aminophenylpyridone acid, 3.84 ml (30 m mol) of chlorotrimethylsilane, 4.2 ml (30 m mol) of triethylamine in 100 ml dichloromethane for 40 min] at −10° C. After the addition, the mixture is allowed to stir at 0° C. for 2 hrs and at room temperature for 12 hrs. To the resulting suspension is added 10 ml isopropanol, stirred for 10 min, and the solids filtered, washed with methanol, ether, and dried to give 2.5 g of 6-[4-(N-Acetyl-alpha-aminoisobutyrylamino)phenyl]-1,2-dihydro-2-oxonicotinic acid.

A suspension of 3.2 g (9 m mol) of the above acylated aminophenylpyridone acid and 25 ml of N,N-dimethylacetamide is stirred at room temperature and 3.24 g (20 m mol) of carbonyldiimidazole is added. The mixture is heated at 60° for 30 min and solution observed. The solution is stirred at room temperature for 1 hr and then allowed to stand overnight. Addition of 40 ml of tetrahydrofuran and 40 ml of ether and cooling gives a solid. Filtration and washing with ether yields 2.08 of product.

D. The silylated derivative of 6-(4-aminophenyl)-1,2-dihydro-2-oxonicotinic acid is prepared by the method of Starting Material E from 57.5 g (0.25 mol) of the acid, 105 ml (0.75 mol) of triethylamine, and 95 ml (0.75 mol) of chlorotrimethylsilane in 1.9 L of dichloromethane.

A solution of 105 g (0.37 mol) of N-carbobenzyloxy-L-glutamine and 1.12 L of N,N-dimethylacetamide is stirred at $-10°$ and 41 ml (0.37 mol) of N-methylmorpholine and 28.6 ml (0.37 mol) of methyl chloroformate is added. The resulting mixture is stirred for 30 min at $-10°$ to $-15°$ and the above silylated acid is added while maintaining the reaction temperature below 5°. The mixture is stirred at 5° for 4 hrs and at room temperature overnight. The mixture is concentrated under reduced pressure to remove the solvents and the residue is treated with ice water. The solid is filtered and washed with water, methanol, and ether and dried to give 106 g of 6-[4-(N-carbobenzyloxy-L-glutaminylamino)phenyl]-1,2-dihydro-2-oxonicotinic acid; $[\alpha]_D^{23} + 17.3°$ (c1, DMSO).

A mixture of 217 g of freshly prepared 31% HBr/acetic acid and 46.8 g of the above N-carbobenzyloxy compound is stirred at room temperature for 3 hrs. A 200 ml portion of ethyl acetate is added and stirring continued for 40 min. The salt is collected by filtration and washed with ethylacetate and ether. The solid is suspended in 300 ml of water and 200 ml of concentrated ammonium hydroxide is added and the mixture stirred for 30 min. The solution is clarified by filtration and the filtrate concentrated to about 100 ml under reduced pressure. The solid is filtered, washed with water, methanol, and ether to give 20.0 g of 6-[4-(L-glutaminylamino)phenyl]-1,2-dihydro-2-oxonicotinic acid; $[\alpha] + 37°$ (c1, DMSO).

A solution of 30.6 g (83 m mol) of 6-[4-(L-glutaminylamino)phenyl]-1,2-dihydro-2-oxonicotinic acid, 56 ml (0.4 mol) of triethylamine, 19 ml (0.2 mol) of acetic anhydride, and 400 ml dimethylformamide is stirred at room temperature for 3 hrs. The reaction solution is evaporated to dryness under reduced pressure and the residue treated with ice and water. The solid is filtered, washed with water, methanol, ether and dried to give 27.6 g of 6-[4-(N-acetyl-L-glutaminylamino)phenyl]-1,2-dihydro-2-oxonicotinic acid; $[\alpha]_D^{23} + 19°$ (c1, DMSO).

$$E_1^1 \; 294 \; \lambda \; 265 \text{ nm} \; pH \; 7$$
$$E_1^1 \; 544 \; \lambda \; 331 \text{ nm} \; pH \; 7$$

Alternative method for the preparation of 6-[4-(N-acetyl-L-glutaminylamino)phenyl]-1,2-dihydro-2-oxonicotinic acid.

A mixture of 309 g (1.64 mol) of acetyl-L-glutamine, 22 g (1.12 mol) of bis(trimethylsilyl)acetamide (BSA) and 5194 ml of tetrahydrofuran was stirred at room temperature for 4 days. Insoluble material was filtered off and 59.4 g (0.81 mol) of dry dimethylformamide was added to the filtrate followed by 20 ml of tetrahydrofuran. The temperature lowered to $-35°$ C. and a solution of 96.7 g (0.81 mol) of thionyl chloride in 522 ml of dichloromethane, kept at $-17°$, was added during a 40 min period while maintaining the reaction temperature at $-34.2°$ to $-36°$ C. for 1 hour.

A mixture of 145.5 g (0.63 mol) of 6-(4-aminophenyl)-1,2-dihydro-2-oxonicotinic acid, 217 g (1.07 mol) of BSA, 654 ml of tetrahydrofuran and 1668 ml of dichloromethane was stirred at room temperature for 3 days, filtered and washed with 920 ml of dichloromethane containing 0.01% of BSA. The filtrate, kept at $-48°$ to $-54°$ C., was added to the above acid chloride during a 1.5 hour period while maintaining the reaction temperature at $-35°$. The reaction mixture was stirred at $-35°$ to $-36°$ C. for 1 hour and at $-33°$ for 14 hours. The reaction mixture was concentrated under reduced pressure at a bath temperature of 34° to 40° C. to a yellow slurry and 3.1 L of ice cold 95% ethanol was added. The mixture was stirred for 30 min and then stored overnight at $-35°$. The suspension was centrifuged and the supernatant was decanted. The residual solid was washed with 1.2 L of 95% ethanol and centrifuged. The process was repeated and the solid obtained was stored at $-30°$ C. This product and that from a duplicate run are combined and treated with 4 L of water in a homogenizer for 30 min. and 28 L of water was added. Stirring was continued for 1.5 hours and the solid was collected by centrifugation and washed with 2 L of water. The solid was stirred in 4 L of water for 30 min and centrifuged. After decantation, the residual solid was washed successively in a similar manner with 3 L of water and 2 portions each of 1.75 L of acetonitrile. The solid was washed with 3 L of ether, filtered and dried to give 439.4 g of 6-[4-(N-acetyl-L-glutaminylamino)phenyl]-1,2-dihydro-2-oxonicotinic acid;

A mixture of 28.0 g (70 m mol) of the above pyridone acid, 17.0 g (0.15 mol) of carbonyldiimidazole, and 200 ml of dimethylformamide is stirred at 50°–55° for 1 hr. The resulting solution is stirred at room temperature overnight and diluted with 500 ml of acetonitrile. The mixture is stirred for 30 min and the solid is filtered, washed with acetonitrile and ether and dried to give 26.4 g of the imidazolide; $[\alpha]_D^{23} + 18.1°$ (c1, DMSO).

E. To a suspension of 5.75 g (25 m mol) 6-(4-aminophenyl)-1,2-dihydro-2-oxonicotinic acid and 175 ml of dichloromethane, 10.2 ml (75 m mol) triethylamine and 9.5 ml (75 m mol) chlorotrimethylsilane are added and the reaction mixture stirred at room temperature for 1 hour. To a solution of 7.86 g (50 m mol) of N-Acetyl-L-proline in 100 ml of dichloromethane at $-10°$ C., 5.5 ml (50 m mol) of N-methylmorpholine and 6.5 ml (50 m mol) of isobutyl chloroformate are added and stirred at $-10°$ C. for $\frac{1}{2}$ hour. To this cold mixed anhydride mixture is added the silylated 6-(4-aminophenyl)-1,2-dihydro-2-oxonicotinic acid and the resulting mixture is stirred for 3 hrs in an ice bath and overnight at room temperature. Next, 25 ml of isopropanol is added to the reaction mixture and stirred. The reaction mixture is evaporated and the residue is triturated with ice and water. The solid is collected by filtration and washed with water, isopropanol and ether to yield 4.82 g of 6-[4-(N-Acetyl-L-prolylamino)phenyl]-1,2-dihydro-2-oxonicotinic acid, m.p. 288°–290° dec. From the filtrate an additional 3.94 g of product is obtained.

A solution of 4.30 g (11.6 m mol) of 6-[4-(N-Acetyl-L-propyl)aminophenyl]-1,2-dihydro-2-oxonicotinic acid, 3.77 g (23.2 m mol) of carbonyldiimidazole and 50 ml of DMF are heated at 50°–58° C. for 1 hour and then stirred at room temperature overnight. To the reaction mixture, 50 ml of tetrahydrofuran and 200 ml of ether are added. The precipitated solid is collected and washed with ether to yield 3.08 g of imidazolide.

F. To a solution of 11.8 g (75 m mol) of N-Acetyl-DL-proline and 10.5 ml (75 m mol) of triethylamine in 150 ml dichloromethane at −15° C., is added 9.75 ml (75 m mol) of isobutyl chloroformate. The reaction mixture is stirred at about −10° C. for 30 min. To this reaction mixture is added a cold solution of 11.5 g (50 m mol) of 6-(4-aminophenyl)-1,2-dihydro-2-oxonicotinic acid and 7.7 ml (55 m mol) triethylamine in 200 ml of N,N-dimethylacetamide, which is stirred while cooling in an ice bath for 3 hrs, then overnight at room temperature. The reaction mixture is evaporated to dryness, the residue is triturated with water, and the solid collected by filtration. The solid is washed with water and acetonitrile and dried to yield 13.2 g of 6-[4-(N-Acetyl-DL-prolylamino)phenyl]-1,2-dihydro-2-oxonicotinic acid, m.p. 279°–281° dec.

A mixture of 7.586 g (20 m mol) of 6-[4-(N-Acetyl-DL-prolyl-amino)phenyl]-1,2-dihydro-2-oxonicotinic acid and 6.48 g (40 m mol) of carbonyldiimidazole in 150 ml tetrahydrofuran is stirred at 52°–56° for 1 hr and overnight at room temperature. The solid product is filtered and washed with tetrahydrofuran and ether. After drying, 7.30 g of the imidazolide is obtained.

G. The silylated derivative of 6-(4-aminophenyl)-1,2-dihydro-2-oxonicotinic acid in 70 ml dichloromethane is added to a mixed anhydride prepared from N-Acetyl-D-asparagine 3.5 g (20 m mol), N-methylmorpholine 2.2 ml (20 m mol) in 50 ml N,N-dimethylacetamide and isobutyl chloroformate 2.9 ml (22 m mol) by stirring at 5° C. for 1 hr and 3 hrs at room temperature. Next 20 ml of isopropanol is added and the reaction mixture evaporated. Water is added to the residue and the mixture filtered. After recrystallization from N,N-dimethylacetamide MeOH, 1.8 g of 6-[4-(N-Acetyl-D-asparaginylamino)phenyl]-1,2-dihydro-2-oxonicotinic acid is obtained, m.p. 265°–266° C.

The above pyridone acid, 1.36 g (3.5 m mol), DMF 20 ml and carbonyldiimidazole, 1.4 g (8.6 m mol), were mixed as described earlier to give 1.6 g of the imidazolide, m.p. 190°–191° C.; $[\alpha]_D^{23} - 390°$ (c1, pH 7).

$$E_1^1 = \begin{matrix} 153 \; \lambda \; 269 \text{ nm} \\ 414 \; \lambda \; 358 \text{ nm} \end{matrix} \text{ pH 7}$$

H. The Tri-Silyl derivative of 6-(4-aminophenyl)-1,2-dihydro-2-oxonicotinic acid is prepared the same as in Starting Material B from 23 g of the acid in 750 ml of dichloromethane, 41.8 ml of triethylamine and 42 ml of chlorotrimethylsilane.

To a suspension of 26.2 g (200 m mol) of N-acetyl-DL-alanine in 500 ml of acetonitrile is added 22 ml (200 m mol) of N-methylmorpholine and the mixture cooled to −15° C. Methyl chloroformate, 17 ml (220 m mol), is added dropwise and stirred for 30 min at −15° C. The silylated mixture above is then added over 20 min at −15° C. The mixture is stirred at 0° for 4 hrs and overnight at room temperature. Isopropanol (60 ml) is added and the product is filtered, washed with dichloromethane then ether and dried affording 33 g of 6-[4-(N-Acetyl-DL-alanylamino)phenyl]-1,2-dihydro-2-oxonicotinic acid; m.p. 279°–298°, $$E_1^1 = \begin{matrix} 327 \; \lambda \; 264 \text{ nm} \\ 630 \; \lambda \; 331 \text{ nm} \end{matrix} \text{ pH 7}$$

The imidazolide derivative (10.8 g) is prepared according to the procedure in Starting Material I, using 10.2 g (30 m mol) of the DL-alanine pyridone acid, 100 ml of DMF and 10.2 g (63 m mol) of carbonyldiimidazole. $[\alpha]_D^{23} - 475°$ (c1, pH 7).

$$E_1^1 = \begin{matrix} 150 \; \lambda \; 268 \text{ nm} \\ 405 \; \lambda \; 358 \text{ nm} \end{matrix} \text{ pH 7}$$

I. To a suspension of 20.14 g (87.5 m mol) of 6-[4-aminophenyl]-1,2-dihydro-2-oxonicotinic acid in 600 ml of dichloromethane is added 36.9 ml (262.5 m mol) of triethylamine followed by 34 ml (262.5 m mol) of chlorotrimethylsilane. The mixture is stirred at room temperature for 45 min.

To a suspension of 22.95 g (175 m mol) of N-acetyl-L-alanine in 440 ml of acetonitrile is added 19.3 ml (175 m mol) of N-methylmorpholine and the mixture cooled to −20° C. Isobutyl chloroformate, 25.0 ml (192.5 m mol), is added dropwise with stirring over 15 min and the mixture is stirred for 40 min at −20° C. To this mixture is added the above prepared silylated pyridone acid, keeping the temperature below −15° C. The mixture is stirred 4 hrs at 5° and overnight at room temperature. Isopropanol (100 ml) is added and the product filtered after 10 min and washed with dichloromethane followed by ether. Drying afforded 24.7 g of 6-[4-(N-Acetyl-L-alanylamino)phenyl]-1,2-dihydro-2-oxonicotinic acid, m.p. 268° d. $[\alpha]_D^{25} - 72°$ (c 0.65, pH 8.4).

To 10 ml of DMF is added 1.0 g of the above L-alanyl pyridone acid (2.91 m mol) and 1.18 g of carbonyldiimidazole and the mixture is heated with stirring to 50° to 60° for 50 min. After cooling to room temperature, 7 ml of dichloromethane and 19 ml of ether are added and the imidazolide derivative is filtered, washed with $CH_2Cl_2$ and ether, and dried in vacuo, giving 1.09 g, m.p. 240°–241° C.; $[\alpha]_D^{23} - 16.3°$ (c1, DMSO).

J. A stirred suspension of 71.3 g (1.32 mol) of sodium methoxide, 500 ml of tetrahydrofuran, and 300 ml of ether is cooled to 0°–5° under nitrogen and a solution of 106.3 g (0.6 mol) of 3-(acetylamino)acetophenone, 96.94 g (1.2 mol) of ethyl formate, 700 ml of dry acetonitrile, and 350 ml of tetrahydrofuran is added during 30 min. The reaction is allowed to warm to room temperature with stirring overnight. The organic solvents are decanted from the solids and the solids dissolved in 2.25 L of water. The pH is adjusted to 9.0 with glacial acetic acid and 84.1 g (1.0 mol) of 2-cyanoacetamide is added. The solution is heated at reflux for 3.5 hrs, cooled, and filtered. The solids are washed with water, acetonitrile, and ether and dried to give 93.1 g of 6-(3-acetylaminophenyl)-1,2-dihydro-2-oxonicotinonitrile; m.p. 326°–328°.

$$E_1^1 = \begin{matrix} 768 \; \lambda \; 350 \text{ nm} \\ 890 \; \lambda \; 242 \text{ nm} \end{matrix} \text{ pH 7}$$

A mixture of 92.5 g (0.37 mol) of 6-(3-acetylaminophenyl)-1,2-dihydro-2-oxonicotinonitrile, 185 g of potassium hydroxide, and 740 ml of water is heated at 105° for 30 hrs. The cooled reaction mixture is poured into 285 ml of concentrated hydrochloric acid and ice. The pH of the suspension is adjusted to 5.0 with aqueous sodium hydroxide solution and the solid filtered, washed with water, and dried to give 81.2 g of 6-(3-aminophenyl)-1,2-dihydro-2-oxonicotinic acid.

$$E_1^1 = \begin{matrix} 650 \; \lambda \; 239 \text{ nm} \\ 825 \; \lambda \; 227 \text{ nm} \end{matrix} \text{ pH 7}$$

The silylated derivative of 6-(3-aminophenyl)-1,2-dihydro-2-oxonicotinic acid is prepared by the method of Starting Material I from 4.37 g (19 m mol) of the acid, 8 ml (57 m mol) of triethylamine, 7.23 ml (57 m mol) of chlorotrimethylsilane and 150 ml of dichloromethane.

A stirred suspension of 4.98 g (38 m mol) of N-acetyl-D-alanine and 100 ml of acetonitrile is cooled to 5° and 4.17 ml (38 m mol) of N-methylmorpholine is added. The resulting solution is cooled to −20° and 2.95 ml (38 m mol) of methyl chloroformate is added. The mixture is stirred at −10°±5° for 1 hr and the above silylated mixture added quickly while maintaining the temperature below −5°. After the addition is complete, the reaction mixture is stirred at 0° for 1 hr and then allowed to warm to room temperature overnight. The dichloromethane is evaporated and 500 ml of water is added. The pH is adjusted to 7.0 with 10% sodium hydroxide solution and extracted with chloroform (3×500 ml). The pH of the aqueous layer is brought to 1.8 with 6 N hydrochloric acid and the solids are filtered washed with water, isopropanol, and ether and dried to give 5.7 g of 6-[3-(N-Acetyl-D-alanylamino)-phenyl]-1,2-dihydro-2-oxonicotinic acid; $[\alpha]_D^{23}+61.5°$ (c1, pH 8.6).

$$E_1^1 = 425 \; \lambda \; 321 \text{ nm} \atop E_1^1 = 239 \; \lambda \; 239 \text{ nm} \text{ pH 7}$$

A mixture of 5.7 g (16.6 m mol) of the above D-alanyl pyridone acid and 40 ml of DMF is stirred at room temperature and 5.7 g (35.2 m mol) of carbonyldiimidazole is added.

The resulting solution is stirred at room temperature for 30 min and at 50°-60° for 2 hrs. The DMF is evaporated under high vacuum at 45° and the residue dissolved in tetrahydrofuran. Addition of ether gives a gum. The solvents are decanted and the gum is solidified by stirring with tetrahydrofuran and ether overnight. The solids are filtered and washed with 1:1 tetrahydrofuran and ether. The solid is suspended in 100 ml of tetrahydrofuran, filtered, washed with tetrahydrofuran and ether, and dried to give 5.7 g of imidazolize; $[\alpha]_D^{23}+10.1°$ (c1, DMF).

K. The silylated derivative of 6-(4-aminophenyl)-1,2-dihydro-2-oxonicotinic acid is prepared as described in Starting Material I from 11.5 g (50 m mol) of the acid, 20.8 ml (0.15 mol) of triethylamine, 19 ml (0.15 mol) of chlorotrimethylsilane, and 250 ml of dichloromethane and added to the following mixed anhydride solution.

A solution of 16.8 g (75 m mol) of N-benzyloxycarbonyl-D-alanine and 200 ml of acetonitrile is stirred at room temperature and 8.2 ml (75 m mol) of N-methylmorpholine is added. The mixture is cooled to −20° and 5.8 ml (75 m mol) of methyl chloroformate is added and the mixture stirred at −15°±5° for 45 min. The above silylated solution is added rapidly while keeping the temperature below −10° and stirred at −10° for 30 min and then allowed to come to room temperature while stirring overnight. Isopropanol (100 ml) is added and the mixture stirred for 30 min and 200 ml of ether is added and the precipitate filtered. The solid is washed with 1:1 dichloromethane ether, and ether and dried. The solid is suspended in water filtered washed with water and dried to give 15.77 g 6-[4-(N-benzyloxycarbonyl-D-alanylamino)phenyl]-1,2-dihydro-2-oxonicotinic acid; $[\alpha]_D^{23}+53.8°$ (c1, 50% methanol/pH 7).

$$E_1^1 = 513 \; \lambda \; 328 \text{ nm} \atop E_1^1 = 246 \; \lambda \; 269 \text{ nm} \text{ pH 7}$$

A suspension of 13.0 g (30 m mol) of the above benzyloxycarbonyl-D-alanyl pyridone acid and 100 ml of 30% HBr in acetic acid is stirred at room temperature for 1.5 hr. Solution is observed in 10 min and then the reaction mixture solidifies. The solid cake is broken up with 450 ml of ethyl acetate and diluted with 500 ml of ether. The precipitate is filtered, washed with 1:1 ethyl acetate ether, ether, and dried. The dry powder is suspended in water and dissolved by raising the pH to 10.7 with the addition of concentrated ammonium hydroxide. The solution is filtered and concentrated and the resulting solids filtered and dried in vacuo to give 8.2 g 6-[4-(D-alanylamino)phenyl]-1,2-dihydro-2-oxonicotinic acid; $[\alpha]_D^{23}-12°$ (c0.83, pH 10.4).

$$E_1^1 = 658 \; \lambda \; 330 \text{ nm} \atop E_1^1 = 364 \; \lambda \; 265 \text{ nm} \text{ pH 7}$$

A suspension of 4.25 g (14.1 m mol) of 6-[4-(D-alanylamino)phenyl]-1,2-dihydro-2-oxonicotinic acid and 500 ml of acetonitrile is stirred at room temperature and 6.97 g (60 m mol) of methyl acetoacetate is added followed by 15 g of molecular sieves (4A Linde, Union Carbide Corporation). The mixture is stirred at room temperature for 18 hrs and then heated at reflux for 24 hrs. The mixture is filtered and the precipitate washed with hot 100 ml of hot acetonitrile. The combined filtrates are evaporated to give 2.0 g of enamine derivative.

A solution of 2.3 g (5.75 m mol) of the above enamine and 20 ml of DMF is stirred at room temperature and 2.3 g (14.2 m mol) of carbonyldiimidazole is added. The solution is stirred at 50°-60° for 1 hr and then at room temperature overnight. The DMF is evaporated under vacuum and the residue dissolved in 40 ml of dichloromethane. The solution is diluted with 100 ml of ethyl acetate and 100 ml of ether. The precipitated solid is filtered, washed with 1:1 ethyl acetate ether and ether and dried to give 2.2 g of imidazolide. L. A mixture of 19.37 g (0.15 mol) of L-pyroglutamic acid, 11.0 ml (0.15 mol) of thionyl chloride, 11.6 ml (0.15 mol) of DMF, and 350 ml of dichloromethane is stirred at 0°-5° for 70 min. This solution is then added to a cold solution of the silylated derivative of 6-(4-aminophenyl)-1,2-dihydro-2-oxonicotinic acid prepared by the method of Starting Material I from 23 g (0.1 mol) of the acid, 42 ml (0.3 mol) of triethylamine, 38 ml (0.3 mol) of chlorotrimethylsilane, and 750 ml of dichloromethane. The reaction mixture is stirred at 0°-5° for 1 hr 45 min and then evaporated to dryness. Methanol is added to the residue and evaporated again. Next 500 ml of methanol and 500 ml of water are added and the solid is collected by filtration, washed with warm methanol and with ether. Drying gives 27.84 g of 6-[4-(L-pyroglutamylamino)phenyl]-1,2-dihydro-2-oxonicotinic acid; $[\alpha]_D^{23}+15.2$ (c1, DMSO).

A mixture of 3.41 g (10 m mol) of the above described acid, 3.24 g (20 m mol) of carbonyldiimidazole, and 50 ml of DMF is stirred at 55° for 45 minutes and then at room temperature overnight. Acetonitrile (200 ml) is added and the mixture allowed to stand for 2 hours. The solids are filtered, washed with acetonitrile and ether and dried to give 2.56 g of the corresponding imidazolide.

M. A solution of 21.9 g (0.15 mol) of L-lysine, 20 ml of pyridine, and 20 ml of water is stirred at room temperature and 40 ml (0.41 mol) of acetic anhydride is added during a 2 hour period. The resulting solution was stirred overnight at room temperature. Another 20 ml of acetic anhydride are added and the solution heated at 40° C. for 2 hours to complete the reaction and the reaction mixture is evaporated to a syrup. The crude product is purified by passing a water solution over a column of 80 g of Amberlite IR-120 resin and eluting with 1500 ml of water. The water is evaporated and the residue crystallized from acetone to afford 15.7 g of N,N'-diacetyl-DL-lysine, m.p. 138°–139° C. A second crop of 10.3 g, m.p. 138°–139° C. is obtained from acetoneacetonitrile.

The silylated derivative of 6-(4-aminophenyl)-1,2-dihydro-2-oxonicotinic acid is prepared by the method of Starting Material I from 2.3 g (10 m mol) of the acid, 3.35 g (33 m mol) of chlorotrimethylsilane, 3.1 g (31 m mol) of triethylamine, and 150 ml of dichloromethane.

A stirred solution of 4.6 g (20 m mol) of N,N'-diacetyl-DL-lysine, 2.02 g (20 m mol) of N-methylmorpholine, and 60 ml of DMF is cooled to −15° and 2.72 g (20 m mol) of isobutylchloroformate is added during a 10 min period while maintaining the temperature at −10° to 15° C. Stirring is continued for 25 minutes at ca. −12° C. and the above silylated mixture is added at −12° to −14° C. over 15 minutes. The resulting mixture is stirred at −10° C. for 10 minutes and then overnight while warming from 5° C. to room temperature as the ice bath melted. Isopropanol (15 ml) is added and the reaction mixture stirred for 2 hrs at 25° C. The solids are filtered, washed with isopropanol, water, and air dried to afford 3.6 g of 6-[4-(N,N'-diacetyl-DL-lysylamino)phenyl]-1,2-dihydro-2-oxonicotinic acid, m.p. 276°–277° dec. Recrystallization from DMF-acetonitrile gave compound with m.p. 277°–278° dec.

A mixture of 2.21 g (5 m mol) of the above acid and 60 ml of DMF is heated to 65° C. and filtered to remove insolubles. The filtrate is treated with 1.62 g (10 m mol) of carbonyldiimidazole and heated at 55° C. for 1 hr and then at room temperature overnight. Acetonitrile (230 ml) is added over a 1 hour period with stirring at room temperature and stirring continued for another 3 hours. The solids are filtered and washed with acetonitrile to give 1.9 g of the corresponding imidazolide, m.p. 210°–221° C.

N. A solution of 100 g (0.76 mol) of L-hydroxyproline and 540 ml of water is cooled to 10° and 297 ml (3.7 mol) of pyridine is added. The temperature is lowered to 5° and 151.2 ml (1.6 mol) of acetic anhydride is slowly added. The reaction is stirred at 0°–5° for 45 min and 81 ml (0.97 mol) of pyridine is added followed by 42.7 ml (0.45 mol) of acetic anhydride. The reaction is stirred overnight in an ice bath allowing the bath to come to room temperature. The reaction is evaporated and the residue is dissolved in ethanol and evaporated to an oily residue. This step is repeated a number of times, and the residue is dissolved in acetone, seeded, and cooled. The white crystals are filtered and recrystallized from ethanol-ether and dried under vacuum at 40° to give 84.8 g of N-acetyl-4-hydroxy-L-proline; $[\alpha]_D^{23} -117°$ (cl, water).

A suspension of 40.0 g (0.173 mol) of 6-(4-aminophenyl)-1,2-dihydro-2-oxonicotinic acid, 72.1 ml (0.517 mol) of triethylamine, and 2800 ml of dichloromethane is stirred at room temperature and 67.8 ml (0.52 mol) of chlorotrimethylsilane is added. The mixture is stirred at room temperature until the solid is almost completely dissolved. A suspension of 63 g (0.362 mol) of N-acetyl-4-hydroxy-L-proline in 650 ml of dichloromethane is cooled to −10° to −15° and 41 ml (0.363 mol) of N-methylmorpholine is added followed by 28.3 ml (0.363 mol) of methyl chloroformate. The reaction is stirred at −15° to −10° for 25 minutes. The reaction temperature is then lowered below −20° and the oxonicotinic acid solution is added in aliquots keeping the temperature below −5°. When the addition is complete, the reaction is stirred in an ice bath overnight, allowing the bath to come to room temperature. The reaction is treated with 30 ml of isopropanol and 30 ml of glacial acetic acid and the resulting mixture is stirred for 10 min at room temperature. The reaction is concentrated and filtered to give 50.1 g of 6-[4-(N-acetyl-4-hydroxy-L-prolylamino)phenyl]-1,2-dihydro-2-oxonicotinic acid $[\alpha]_D^{23} -60.5°$ (cl, pH 7).

A solution of 29.9 g (0.078 mol) of the above pyridone acid, 120 ml of pyridine, and 60 ml of acetic anhydride is stirred overnight at room temperature. The solution is cooled and upon adding methanol, a precipitate forms. The mixture is cooled and then filtered and the solid is air dried. The solid is recrystallized from 1800 ml of 20% water in methanol and dried at 50° under vacuum to give 21.1 g of 6-[4-[N-acetyl-4-(acetyloxy)-L-prolylamino]phenyl]-1,2-dihydro-2-oxonicotinic acid; $[\alpha]_D^{23} +17.3°$ (cl, 75% DMF/pyridine).

A mixture of 5 g (11.7 mmol) of the above oxonicotinic acid, 5 g 30.8 mmol) of carbonyldimidazole, 150 ml of acetonitrile, and 5 ml of N,N-dimethylacetamide is stirred at 50° for 2¾ hours. The solid is filtered, washed with acetonitrile and ether, and dried to give 5.23 g of 6-[4-[N-acetyl-4-(acetyloxy)-L-prolyl]amino]phenyl]-1,2-dihydro-2-oxonicotinic acid imidazolide.

O. Reaction of 6-[4-(N-acetyl-4-hydroxy-L-prolylamino)phenyl]-1,2-dihydro-2-oxonicotinic acid with formic acid and acetic anhydride gives 6-[4-[N-acetyl-4-(formyloxy)-L-prolyl]amino]phenyl-1,2-dihydro-2-oxonicotinic acid; $[\alpha]_D^{23} +19.2°$ (cl, DMSO).

A suspension of 10.8 g (35 mmol) of the above oxonicotinic acid 17.0 g (0.105 mol) of carbonyliimdazole, 400 ml of acetonitrile and 20 ml of N,N-dimethylacetamide is stirred at 65° for 2 hours. The solution is concentrated and the yellow precipitate is filtered to give 6.9 g of 6-[4-[N-acetyl-4-(formyloxy)-L-prolyl]amino]phenyl-1,2-dihydro-2-oxonicotinic acid imidazolide.

P. A suspension of 4 g (10.4 mmol) of 6-[4-(N-acetyl-4-hydroxy-L-prolylamino)phenyl]-1,2-dihydro-2-oxonicotinic acid, 4 ml (31 mmol) of propionic anhydride, and 25 ml of pyridine is stirred at room temperature for 1 hr. The resulting solution is allowed to stand overnight at room temperature and methanol is added. The solid is filtered, washed, and dried to give 2.2 g of 6-[4-[N-acetyl-4-(1-oxopropoxy)-L-prolylamino]-phenyl]-1,2-dihydro-2-oxonicotinic acid. Another 2.0 g are obtained by evaporating the filtrate and treating the residue with water. The pH is adjusted to 2.5 with 1 N hydrochloric acid and cooled and the solid is filtered, washed with water and air dried.

A mixture of 2.2 g (5 mmol) of the above pyridone acid, 2.2 g (13.5 mmol) of carbonyldiimidazole, 70 ml of acetonitrile, and 2 ml of dimethylformamide is stirred at 55° for 1.5 hour and at room temperature for 4.5 hrs. The solid is filtered, washed with acetonitrile and ether and dried to give 2.02 g of 6-[4-[N-acetyl-4-(1-oxopropoxy-L-prolylamino]phenyl]-1,2-dihydro-2-oxonicotinic acid imidazolide.

Q. A suspension of 3.09 g (21.6 mmol) of N-methyl-5-oxo-L-proline, 1.58 ml (21.6 mmol) thionyl chloride, 1.67 ml (21.6 mmol) dimethylformamide, and 50 ml of dichloromethane is stirred with ice bath cooling for 70 min. Simultaneously, a suspension of 3.31 g (14.4 mmol) of 6-(4-aminophenyl)-1,2-dihydro-2-oxonicotinic acid, 100 ml dichloromethane, 6.05 mol (43.2 mmol) triethylamine, and 5.48 ml (4.32 mmol) chlorotrimethylsilane is stirred at room temperature for 1 hour. The silylated mixture is cooled with an ice bath and the acid chloride complex is added. The reaction mixture is stirred in an ice bath for 6 hrs and at room temperature overnight. The reaction mixture is treated with 50 ml of 2-propanol and is filtered to give 3.70 g of 6-[4-(N-methyl-5-oxo-L-propyl)amino]phenyl-1,2-dihydro-2-oxonicotinic acid; $[\alpha]_D^{23} + 11.8°$ (cl, DMSO).

A suspension of 3.44 g (9.68 mmol) of the above pyridone acid, 3.14 g (19.36 mmol) of carbonyldiimidazole, and 35 ml of dimethylformamide is stirred at 53°–57° for 45 min and at room temperature overnight. After addition of 100 ml of acetonitrile, the solid is collected by filtration. The solid is washed with acetonitrile and ether to give 2.51 g of 6-[4-(N-methyl-5-oxo-L-propyl)amino]phenyl-1,2-dihydro-2-oxonicotinic acid imidazole; $[\alpha]_D^{23} + 9.8°$ (cl, DMSO).

R. A solution of 29.0 g (70 mmol) of N,N'-bis(benzyloxycarbonyl)-L-lysine [Helv. Chem. Acta, 41, 1778 (1958)] in 200 ml of dichloromethane is stirred at −10° and 7.2 g (70 mmol) of N-methylmorpholine is added. The temperature is lowered to −14° and 9.55 g (70 mmol) of isobutyl chloroformate is added dropwise over a period of 10 min and stirring is continued at −14° to −11° for 40 min. A suspension of 8.0 g (35 mmol) of 6-(4-aminophenyl)-1,2-dihydro-2-oxonicotinic acid, 10.5 g (35 mmol) of triethylamine and 200 ml of dichloromethane is stirred at 5° and 12.0 g (35 mmol) of chlorotrimethylsilane is added. After 1 hr at room temperature this solution is added over a period of 30 min at −12° to −14° to the mixed anhydride formed above. After 3 hrs at 0°, the solution is allowed to stir overnight at room temperature. The reaction mixture is filtered and the filtrate is stirred with 15 ml of isopropanol for 30 min. The resulting yellow precipitate is filtered, washed, and dried to give 16.6 g of 6-[4-(N,N'-bis(benzyloxycarbonyl)-L-lysylamino)phenyl]-1,2-dihydro-2-oxonicotinic acid; mp 199°–200°, $[\alpha]_D^{23} + 24.2°$ (cl, DMSO).

A solution of hydrogen bromide in glacial acetic acid (30%, 60 ml) is stirred at room temperature and 16.3 g (26 mmol) of the above pyridone acid is added over 10 min and stirring continued for 15 min. A solid separates from the solution during a 2 hr period, and the mixture is diluted with 300 ml of ethyl acetate. The mixture is stirred for 2 hrs and filtered giving 10.9 g of 6-[4-(L-lysylamino)phenyl]-1,2-dihydro-2-oxonicotonic acid dihydrobromide as yellow crystals; mp 291°–292° dec; $[\alpha]_D^{23} + 39.4°$ (cl, DMSO).

An aqueous solution of the above dihydrobromide is stirred at room temperature and 75 ml of concentrated ammonium hydroxide is added. The yellow crystalline precipitate is filtered after stirring for 2 hrs to give 6.9 g of 6-[4-(L-lysylamino)phenyl]-1,2-dihydro-2-oxo-oxonicotinic acid; mp 281°–282° dec, $[\alpha]_D^{23} + 41.5°$ (cl, pH 7).

The above pyridone acid (6.7 g, 18.7 mmol) is suspended in 60 ml of water and treated with 10 ml of acetic anhydride with stirring. After 3 min a yellow precipitate begins to separate from the solution. Another 2.5 ml of acetic anhydride is added and stirring is continued for 4 hrs at room temperature. The solid is filtered, washed, and dried to give 7.8 g of 6-[4-(N,N'-diacetyl-L-lysylamino)phenyl]-1,2-dihydro-2-oxonicotinic acid; mp 263°–264° dec, $[\alpha]_D^{23} - 63°$ (cl, pyridine).

A suspension of 7.3 g (16.5 mmol) of the above pyridone acid, 5.4 g (33 mmol) of carbonyldiimidazole, and in 75 ml of N,N-dimethylformamide is stirred at 55° for 40 min and overnight at room temperature. Acetonitrile (350 ml) is added dropwise over 30 min and the resulting precipitate is stirred for 2.5 hrs. The solid is filtered and washed with 100 ml of acetonitrile to give 7.4 g of 6-[4-(N,N'-diacetyl-L-lysylamino)phenyl]-1,2-dihydro-2-oxonicotinic acid immidazolide; mp 219°–220° dec, $[\alpha]_D^{23} + 21°$ (cl, DMSO).

S. A suspension of 172.5 g (0.75 mol) of 6-(4-aminophenyl)-1,2-dihydro-2-oxonicotinic acid, 312 ml (2.23 mol) of triethylamine, and 11.8 L of dichloromethane is stirred at 10° and 290 ml (2.28 mol) of chlorotrimethylsilane is slowly added. The resulting mixture is stirred overnight at room temperature. A mixture of 273 g (1.58 mol) of N-acetyl-4-hydroxy-L-proline and 3.5 L of dichloromethane is stirred at −15° and 177.5 ml (1.61 mol) of N-methylmorpholine is added during a 20 min period followed by 250 ml of dichloromethane as a wash. The mixture is stirred at −13° for 15 min and 125.5 ml (1.62 mol) of methyl chloroformate is added over a 25 min period at −14° followed by 150 ml of dichloromethane as a wash. The mixture is stirred at −15° for 40 min and the above silylated nicotinic acid is added over a period of 60 min at −17° followed by 500 ml of dichloromethane as a rinse. The mixture is stirred for 1 hr and 40 min as the temperature rose to 1°. The mixture is stirred overnight with ice bath cooling as the temperature rose to 16° and 135 ml of glacial acetic acid is added followed by 135 ml of isopropanol. The reaction mixture is concentrated to 4 L under reduced pressure and the solid filtered, washed with dichloromethane and dried to give 245 g of 6-[4-(N-acetyl-4-hydroxy-L-prolylamino)phenyl]-1,2-dihydro-2-oxonicotinic acid.

A mixture of 50.0 g (0.31 mol) of the above pyridone acid 72.2 ml (0.754 mol) of 2-methoxypropene, and 190 ml of N,N-dimethylacetamide is stirred at room temperature overnight. The solution is clarified by filtration and the filtrate is diluted with 400 ml of acetonitrile and stirred at room temperature for 1.5 hr. The solid is filtered, washed with acetonitrile and ether and dried briefly under vacuum to give 46 g of product. The unstable product was converted to the imidazolide below. A mixture of the above product (46 g), 42.2 g (0.26 mol) of carbonyldiimidazole, 6 ml of N,N-dimethylacetamide, and 650 ml of acetonitrile is stirred at 50° for 40 min and cooled to 0°–5°. The solid is filtered, washed with acetonitrile and ether and dried to give 45.0 g of 6-[4-[N-acetyl-4-(2-methoxy-1-methylethoxy)-L-prolylamino]phenyl]-1,2-dihydro-2-oxonicotinic acid imidazolide; $[\alpha]_D^{23} + 15°$ (cl, DMSO).

T. A solution of 4.2 g (15 mmol) of N-carbobenzoxy-D-glutamine and 50 ml of N,N-dimethylacetamide is stirred at −12° and 1.65 ml (15 mmol) of N-methylmorpholine and 1.2 ml (15 mmol) of methyl chloroformate are added. The mixture is stirred at −12° for 15 min. A suspension of 2.3 g (10 mmol) of 6-(4-aminophenyl)-1,2-dihydro-2-oxonicotinic acid is stirred in 75 ml dichloromethane at room temperature and is silylated with 3.8 ml (30 mmol) of chlorotrimethylsilane and 4.2 ml (30 mmol) of triethylamine. The solution of the silylated material is cooled to 0°–5° and is then added to the solution of the above mixed anhydride. The reaction mixture is stirred at −7° for 1 hr, then at 0°–5° for 4 hrs and at room temperature for 16 hrs and 30 ml of isopropanol is added. The bulk of the solvents is removed at reduced pressure and the residue is diluted with 250 ml cold water. The precipitate is collected, washed with cold water and dried to give 4.4 g of 6-[4-(N-carbobenzoxy-D-glutaminylamino)phenyl]-1,2-dihydro-2-oxonicotinic acid as a yellow solid; mp 250°–252° dec; $[\alpha]_D^{23}$ −13.3° (cl, DMSO).

A mixture of 4.2 g (8.5 mmol) of the above product and 30 ml of a solution of 30% hydrogen bromide in acetic acid is stirred at room temperature for 2 hrs. A 30 ml portion acetic acid is added and the mixture is stirred for an additional 30 min. The precipitated hydrobromide salt of the product is collected, washed with ethyl acetate and water. The filtercake is dissolved in 70 ml water and 20 ml of concentrated ammonium hydroxide solution is added. The solution is filtered and then concentrated to ca. 20 ml at reduced pressure. The precipitate is collected, washed with cold water and ether and dried to give 2.6 g of 6-[4-(D-glutaminylamino)phenyl]-1,2-dihydro-2-oxonicotinic acid; mp 310°–312° dec.

A mixture of 2.5 g (7 mmol) of the above acid and 50 ml of dimethylformamide is stirred at room temperature, and 4.9 ml (35 mmol) of triethylamine and 1.7 ml (18 mmol) of acetic anhydride are added. The mixture is stirred at room temperature for 3 hrs and the solvent is removed at reduced pressure. The residue is triturated with cold water and the solid is collected, washed with water and ether, and dried to give 2.4 g of 6-[4-(N-acetyl-D-glutaminylamino)phenyl]-1,2-dihydro-2-oxonicotinic acid as a yellow solid; mp 253°–255° dec, $[\alpha]_D^{23}$ −17.8° (cl, DMSO).

A mixture of 2.3 g (5.75 mmol) of the above nicotinic acid, 2.6 g (16 mmol) of carbonyldiimidazole, and 25 ml of dimethylformamide is stirred at 50° for 45 min and at room temperature overnight. The mixture is diluted with 75 ml of acetonitrile and the solid is collected, washed with acetonitrile, and dried to give 1.9 g of 6-[4-(N-acetyl-D-glutaminylamino)phenyl]-1,2-dihydro-2-oxonicotinic acid imidazolide as a yellow solid; mp 208°–212° dec, $[\alpha]_D^{23}$ −16.4° (cl, DMSO).

U. A suspension of 2.36 g (6.6 mmol) of 6-[4-(L-glutaminylamino)phenyl]-1,2-dihydro-2-oxonicotinic acid in 50 ml of water is stirred at room temperature. The pH is adjusted to 9 with 1 N sodium hydroxide and 50 ml of t-butyl alcohol is added. The reaction is stirred at room temperature and treated dropwise over ½ hr with 1.76 ml (8.0 mmol) of di-tert-butyl dicarbonate. The reaction is stirred at room temperature for 1 hr, and the solvents are removed under reduced pressure. The residue is suspended in water and acidified with solid citric acid. The precipitate is filtered, washed with water, ethanol, ether, and dried to give 2.3 g of 6-[4-(N-t-butoxycarbonyl-L-glutaminylamino)phenyl]-1,2-dihydro-2-oxonicotinic acid;

A suspension of 2.2 g (6.1 mmol) of the above nicotinic acid, 2.43 g (15 mmol) of carbonyldiimidazole and 25 ml of N,N-dimethylformamide is stirred at 50°–60° for 2 hrs. The solvent is removed under reduced pressure and the residue heated in acetonitrile until a precipitate develops. The mixture is diluted with ether, filtered, washed with acetonitrile/ether (1:1), ether, and dried to give 2.06 g of 6-[4-(N-t-butoxycarbonyl-L-glutaminylamino)phenyl]-1,2-dihydro-2-oxonicotinic acid and imidazolide.

We claim:
1. A compound of the formula

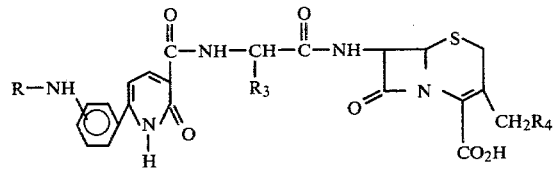

and pharmaceutically acceptable salts thereof; wherein R is

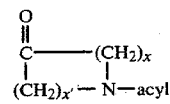

or $R_1$-[$R_5$N-acyl]$_n$; x is an integer of from one to five; x′ is zero, one or two, $R_1$ is hydrogen, lower alkyl, benzyl or

wherein $R_2$ is hydrogen, amino, or lower alkyl group of from one to four carbon atoms, optionally substituted by from one to three chlorine or fluorine atoms, $R_5$ is hydrogen or lower alkyl and N-acyl is an aminoacyl moiety derived from a carboxylic acid of from two to ten carbon atoms, optionally substituted by from one to three of the following groups, hydroxyl, carboxyl,

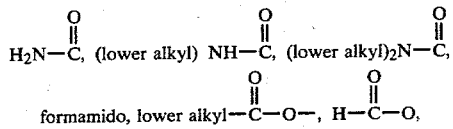

amino, lower alkylamido, carbamido, carbonyl oxygen, lower alkoxy, lower alkylthio, or sulfonic acid, n is an integer of from one to four; $R_3$ is phenyl, 4-hydroxyphenyl, 2-thienyl or cyclohexa-1,4-dien-1-yl and $R_4$ is acetoxy, carbamoyloxy, or a heterocyclicthio group where the heterocyclic moiety is unsubstituted or substituted by a methyl group and the heterocycle is a thiadiazolyl, triazolyl or tetrazolyl group or the heterocyclicthio group has the formula

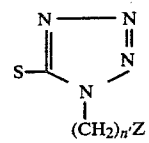

wherein Z is

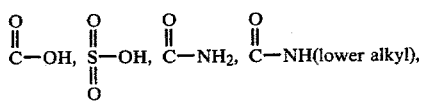

-continued

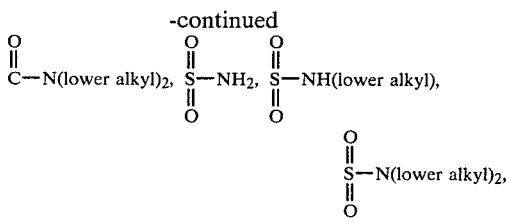

or CH$_2$-OH and n' is an integer of from one to four.

2. The compounds of claim 1 wherein R-NH is in the para position.

3. The compounds of claim 2 wherein the optically active R$_1$ aminoacyl fragment is in the D form.

4. The compounds of claim 2 wherein NH-acyl if D-alanyl, L-glutaminyl, D-glutaminyl, L-pyroglutamyl or L-lysyl.

5. The compounds of claim 4 wherein R$_2$ is a carbon fragment of from one to two carbon atoms.

6. The compounds of claim 5 wherein R$_3$ is phenyl or p-hydroxyphenyl.

7. The compounds of claim 6 wherein R$_4$ is acetoxy.

8. The compounds of claim 1 having the name N-[6-[4-(N-acetyl-D-alanylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid and pharmaceutically acceptable salts thereof.

9. The compounds of claim 1 having the name N-[6--[4-(N-acetyl-L-prolylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

10. The compounds of claim 1 having the name N-[6-[4-(N-acetyl-DL-alanylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

11. The compounds of claim 1 having the name N-[6-[4-(N-acetyl-D-alanylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

12. The compounds of claim 1 having the name N-[6-[4-(N-acetyl-L-alanylamino)phenyl]-1,2-dihydro-2-oxonicotinyl]-6-[D-2-amino-2-phenylacetamido]-3-acetoxymethyl-3-cephem-4-carboxylic acid and pharmaceutically acceptable salts thereof.

13. The compounds of claim 1 having the name N-[6-[4-(L-pyroglutamylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

14. The compounds of claim 1 having the name N-[6-[4-(L-pyroglutamylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

15. The compounds of claim 1 having the name N-[6-[4-(N-acetyl-D-alanylamino)phenyl]-1,2-dihydro-2-oxonicotinyl]-7-[D-2-amino-2-(4-hydroxyphenyl)acetamido]-3-acetoxymethyl-3-cephem-4-carboxylic acid and pharmaceutically acceptable salts thereof.

16. The compounds of claim 1 having the name N-[6-[4-(N-acetyl-L-glutaminylamino)phenyl]-1,2-dihydro-2-oxonicotinyl]-7-[D-2-amino-2-phenylacetamido]-3-[[(1-methyl-1-H-tetrazol-5-yl)thio]methyl]-3-cephem-4-carboxylic acid and pharmaceutically acceptable salts thereof.

17. The compounds of claim 1 having the name N-[6-[4-(N-acetyl-Dl-alanylamino)phenyl]-1,2-dihydro-2-oxonicotinyl]-7-[D-2-amino2-phenylacetamido]-3-carbamoyloxymethyl-3-cephem-4-carboxylic acid and pharmaceutically acceptable salts thereof.

18. The compounds of claim 1 having the name N-[6-[4-(N-acetyl-alpha-aminoisobutyrylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

19. The compounds of claim 1 having the name N-[6-[4-(N-acetyl-L-propylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

20. The compounds of claim 1 having the name N-[6-[4-(N-acetyl-D-asparaginylamino)phenyl-1,2-dihydro-2-oxonicotinyl]-7-[D-2-amino-2-phenylacetamido]-3-acetoxymethyl-3-cephem-4-carboxylic acid and pharmaceutically-acceptable salts thereof.

21. The compounds of claim 1 having the name N-[6-[4-(N-acetyl-L-glutaminylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

22. The compounds of claim 1 having the name N--[6-[4-(N-acetyl-L-alanylamino)phenyl]-1,2-dihydro-2-oxonicotinyl]-7-[D-2-amino-phenylacetamido]-3-[((5-methyl-1,3,4-thiadiazoyl-2-yl]thio)methyl]-3-cephem-4-carboxylic acid and pharmaceutically acceptable salts thereof.

23. The compounds of claim 1 having the name N-[6--[4-(L-pyroglutamylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid and pharmaceutically acceptable salts thereof.

24. The compounds of claim 1 having the name N-[6-[4-(N-acetyl-DL-prolylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

25. The compounds of claim 1 having the name N-[6--[4-(N-acetyl-DL-alanylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

26. The compounds of claim 1 having the name N-[6--[4-(N-acetyl-D-alanylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

27. The compounds of claim 1 having the name N-[6--[4-(N-acetyl-L-alanylamino)phenyl]-1,2-dihydro-2-oxonicotinyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

28. The compounds of claim 1 having the name N-[6-[4-(N-acetyl-L-glutaminylamino)phenyl]-1,2-dihydro-2-oxonicotinyl]-7-[D-2-amino-2-phenylacetamido]-3-

[[(1-carboxymethyl-1H-tetrazol-5-yl)thio]methyl]-3-cephem-4-carboxylic acid and pharmaceutically acceptable salts thereof.

29. The compounds of claim 1 having the name N-[6-[4-(N-acetyl-DL-alanylamino)phenyl]-1,2-dihydro-2-oxonicotinyl]-7-[D-2-amino-2-phenylacetamido]-3-[([4-methyl-1,3,4-thiadiazoyl-2-yl]thio)methyl]-3-cephem-4-carboxylic acid and pharmaceutically acceptable salts thereof.

30. The compounds of claim 1 having the name N-[6-[4-(N-acetyl-D-asparaginylamino)phenyl]-1,2-dihydro-2-oxonicotinyl]-7-[D-2-phenylacetamido]-3-[[(1-methyl-1H-tetrazol-5-yl)thio]methyl]-3-cephem-4-carboxylic acid and pharmaceutically acceptable salts thereof.

31. The compounds of claim 1 having the name N-[6-[4-(N-acetyl-D-alanylamino)phenyl]-1,2-dihydro-2-oxonicotinyl]-7-[D-2-amino-2-phenylacetamido]-3-carbamoyloxymethyl-3-cephem-4-carboxylic acid and pharmaceutically acceptable salts thereof.

32. The compounds of claim 1 having the name N-[6-[4-(N-acetyl-D-alanylamino)phenyl]-1,2-dihydro-2-oxonicotinyl]-7-[D-2-amino-2-(4-hydroxyphenyl)acetamido]-3-[[(1-methyl-1H-tetrazol-5-yl)thio]methyl]-3-cephem-4-carboxylic acid and pharmaceutically acceptable salts thereof.

33. The compounds of claim 1 having the name N-[-6-[4-(N,N'-diacetyl-DL-lysylamino)phenyl]-1,2-dihydro-2-oxonicotinyl]-7-[D-2-phenylacetamido]-3-[[(1-methyl-1H-tetrazol-5-yl)thio]methyl]-3-cephem-4-carboxylic acid and pharmaceutically acceptable salts thereof.

34. The compounds of claim 1 having the name N-[6-[4-(N,N'-diacetyl-DL-lysylamino)phenyl]-1,2-dihydro-2-oxonicotinyl]-7-(D-2-amino-2-phenylacetamido]-3-acetoxymethyl-3-cephem-4-carboxylic acid and pharmaceutically acceptable salts thereof.

35. The compounds of claim 1 having the name N-[6-[3-(N-acetyl-D-alanylamino)phenyl]-1,2-dihydro-2-oxonicotinyl]-7-[D-2-amino-2-phenylacetamio]-3-acetoxymethyl-3-cephem-4-carboxylic acid and pharmaceutically acceptable salts thereof.

36. The compounds of claim 1 having the name N-[6-[4-(D-alanylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

37. A compound of claim 1 having the name N-[6-[4-(N-Acetyl-4-hydroxy-L-prolylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid and pharmaceutically acceptable salts thereof.

38. A compound of claim 1 having the name N-[6-[4-(N-Acetyl-4-hydroxy-L-prolylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

39. A compound of claim 1 having the name N-[6-[4-[N-Acetyl-4-(acetyloxy)-L-prolylamino]phenyl]-1,2-dihydro-2-oxoniotinyl]-7-[D-2-amino-2-phenylacetamido]-3-acetoxymethyl-3-cephem-4-carboxylic acid and pharmaceutically acceptable salts thereof.

40. A compound of claim 1 having the name N-[6-[4-[N-Acetyl-4-(formyloxy)-L-prolylamino]phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

41. A compound of claim 1 having the name N-[6-[4-[N-Methyl-5-oxo-L-prolylamino]phenyl]-1,2-dihydro-2-oxo-nicotinyl]-7-[D-2-amino-2-phenylacetamido]-3-acetoxymethyl-3-cephem-4-carboxylic acid and pharmaceutically acceptable salts thereof.

42. A compound of claim 1 having the name N-[6-[4-(N,N'-Diacetyl-L-lysylamino)phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

43. A compound of claim 1 having the name N-[6-[4-[N-Acetyl-4-(1-oxopropoxy)-L-prolylamino]-phenyl]-1,2-dihydro-2-oxonicotinyl]-7-[D-2-amino-2-phenylacetamido]-3-[[(1-carboxymethyl-1-H-tetrazol-5-yl)thio]methyl]-3-cephem-4-carboxylic acid and pharmaceutically acceptable salts thereof.

44. A compound of claim 1 having the name N-[6-[4-(N-Acetyl-D-glutaminylamino)phenyl]-1,2-dihydro-2-oxonicotinyl]-7-[D-2-amino-2-phenylacetamido]-3-[[(1-carboxymethyl-1H-tetrazol-5-yl)thio]methyl]-3-cephem-4-carboxylic acid and pharmaceutically acceptable salts thereof.

45. A compound of claim 1 having the name N-[6-[4--(L-Glutaminylamino)phenyl]-1,2-dihydro-2-oxonicotinyl]-7-[D-2-amino-2-phenylacetamido]-3-[[(1-carboxylmethyl-1H-tetrazol-5-yl)thio]methyl]-3-cephem-4-carboxylic acid and pharmaceutically acceptable salts thereof.

46. A compound of claim 1 having the name N-[6-[4-[N-Acetyl-4-(1-oxopropoxy)-L-prolylamino]-phenyl]-1,2-dihydro-2-oxonicotinyl]-7-[D-2-amino-2-phenylacetamido]-3-acetoxymethyl-3-cephem-4-carboxylic acid and pharmaceutically acceptable salts thereof.

47. A compound of claim 1 having the name N-[6-[4--[N-Acetyl-4-(1-oxopropoxy)-L-prolylamino]phenyl]-1,2-dihydro-2-oxonicotinyl]-7-[D-2-amino-2-phenylacetamido]-3-[[(1-methyl-1H-tetrazol-5-yl)thio]-methyl]-3-cephem-4-carboxylic acid and pharmaceutically acceptable salts thereof.

48. A compound of claim 1 having the name N-[6-[4--(N-Acetyl-D-alanylamino)phenyl]-1,2-dihydro-2-2-oxonicotinyl]-7-[D-2-amino-2-phenylacetamido]-3-[[[1-(2-carboxyethyl)-1H-tetrazol-5-yl]thio]methyl]-3-cephem-4-carboxylic acid and pharmaceutically acceptable salts thereof.

49. A compound of claim 1 having the name N-[6-[4-(N-Acetyl-L-glutaminylamino)phenyl]-1,2-dihydro-2-oxonicotinyl]-7-[D-2-amino-2-phenylacetamido]-3-[[(1-sulfomethyl-1H-tetrazol-5-yl)thio]methyl]-3-cephem-4-carboxylic acid and pharmaceutically acceptable salts thereof.

50. A compound of claim 1 having the name N-[6-[4-(N-Acetyl-L-glutaminylamino)phenyl]-1,2-dihydro-2-oxonicotinyl]-7-[D-2-amino-2-(4-hydroxyphenyl)acetamido]-3-[[(1-methyl-1H-tetrazol-5-yl)thio]methyl]-3-cephem-4-carboxylic acid and pharmaceutically acceptable salts thereof.

51. A pharmaceutical composition comprising from 30 mg to 1000 mg of a compound of claim 1 and a pharmaceutical carrier.

52. A method for treating infections which comprises administering the pharmaceutical composition of claim 51.

* * * * *